(12) United States Patent
Giddings et al.

(10) Patent No.: US 9,435,868 B2
(45) Date of Patent: Sep. 6, 2016

(54) MAGNETO-RESISTIVE EFFECT DEVICE, MAGNETIC HEAD GIMBAL ASSEMBLY, MAGNETIC RECORDING/REPRODUCTION DEVICE, STRAIN SENSOR, PRESSURE SENSOR, BLOOD PRESSURE SENSOR, AND STRUCTURAL HEALTH MONITORING SENSOR

(71) Applicant: Kabushiki Kaisha Toshiba, Minato-ku (JP)

(72) Inventors: Devin Giddings, Eindhoven (NL); Hideaki Fukuzawa, Kanagawa-ken (JP); Yoshihiko Fuji, Kanagawa-ken (JP); Michiko Hara, Kanagawa-ken (JP); Hiromi Yuasa, Kanagawa-ken (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 16 days.

(21) Appl. No.: 14/659,762

(22) Filed: Mar. 17, 2015

(65) Prior Publication Data
US 2015/0185296 A1 Jul. 2, 2015

Related U.S. Application Data

(62) Division of application No. 13/246,069, filed on Sep. 27, 2011, now Pat. No. 9,032,808.

(30) Foreign Application Priority Data

Mar. 24, 2011 (JP) ................................ 2011-066017

(51) Int. Cl.
*G01R 33/09* (2006.01)
*A61B 5/021* (2006.01)
(Continued)

(52) U.S. Cl.
CPC ......... *G01R 33/091* (2013.01); *A61B 5/02108* (2013.01); *G01R 33/093* (2013.01);
(Continued)

(58) Field of Classification Search
None
See application file for complete search history.

(56) References Cited

U.S. PATENT DOCUMENTS 5,891,586 A * 4/1999 Hasegawa ............ G11B 5/3903
428/811.2
6,694,822 B1 * 2/2004 Ganapathi ............... G01L 1/125
73/728
(Continued)

FOREIGN PATENT DOCUMENTS

JP 8-264861 10/1996
JP 2002-299725 10/2002
(Continued)

OTHER PUBLICATIONS

M. Löhndorf, et al., "Characterization of magnetostrictive TMR pressure sensors by MOKE", Journal of Magnetism and Magnetic Materials, vol. 316, 2007, pp. e223-e225.
(Continued)

*Primary Examiner* — Craig A. Renner
(74) *Attorney, Agent, or Firm* — Oblon, McClelland, Maier & Neustadt, L.L.P

(57) ABSTRACT

According to one embodiment, a magneto-resistive effect device, includes a stacked body stacked on a substrate, a pair of first electrodes that feeds current to the stacked body, a strain introduction member, and a second electrode for applying a voltage to the strain introduction member. The stacked body includes a first magnetic layer that includes one or more metals selected from the group consisting of iron, cobalt, and nickel, a second magnetic layer stacked on the first magnetic layer, having a composition that is different from the first magnetic layer, and a spacer layer disposed between the first magnetic layer and the second magnetic layer.

24 Claims, 24 Drawing Sheets

(51) Int. Cl.
- *G01B 7/16* (2006.01)
- *G11B 5/39* (2006.01)
- *H01L 43/08* (2006.01)
- *H01F 10/30* (2006.01)
- *A61B 5/022* (2006.01)
- *H01F 10/32* (2006.01)

(52) U.S. Cl.
CPC ............ *G11B5/3906* (2013.01); *G11B 5/399* (2013.01); *H01F 10/30* (2013.01); *H01L 43/08* (2013.01); *A61B 5/022* (2013.01); *A61B 2562/0247* (2013.01); *G11B 2005/3996* (2013.01); *H01F 10/325* (2013.01); *H01F 10/3254* (2013.01); *H01F 10/3259* (2013.01)

(56) References Cited

U.S. PATENT DOCUMENTS

| | | |
|---|---|---|
| 8,760,154 B2 | 6/2014 | Giddings et al. |
| 8,933,909 B2 | 1/2015 | Giddings et al. |
| 8,958,574 B2 | 2/2015 | Fukuzawa et al. |
| 8,973,446 B2 | 3/2015 | Fukuzawa et al. |
| 9,032,808 B2 * | 5/2015 | Giddings ............... G11B 5/399 73/779 |
| 2005/0088789 A1 | 4/2005 | Hou et al. |
| 2011/0295128 A1 | 12/2011 | Yuasa et al. |
| 2014/0090486 A1 | 4/2014 | Fuji et al. |
| 2014/0137668 A1 | 5/2014 | Fukuzawa et al. |

FOREIGN PATENT DOCUMENTS

| | | |
|---|---|---|
| JP | 2003-37312 | 2/2003 |
| JP | 2004-259914 | 9/2004 |
| JP | 2006-100574 | 4/2006 |
| JP | 2007-95186 | 4/2007 |
| JP | 2007-165572 | 6/2007 |
| JP | 2008-112496 | 5/2008 |
| JP | 2009-289390 | 12/2009 |

OTHER PUBLICATIONS

Office Action issued Mar. 15, 2013 in Japanese Application No. 2011-066017 (w/English translation).

Japanese Office Action issued Apr. 14, 2014, in Japan Patent Application No. 2013-096808 (w/English translation).

* cited by examiner

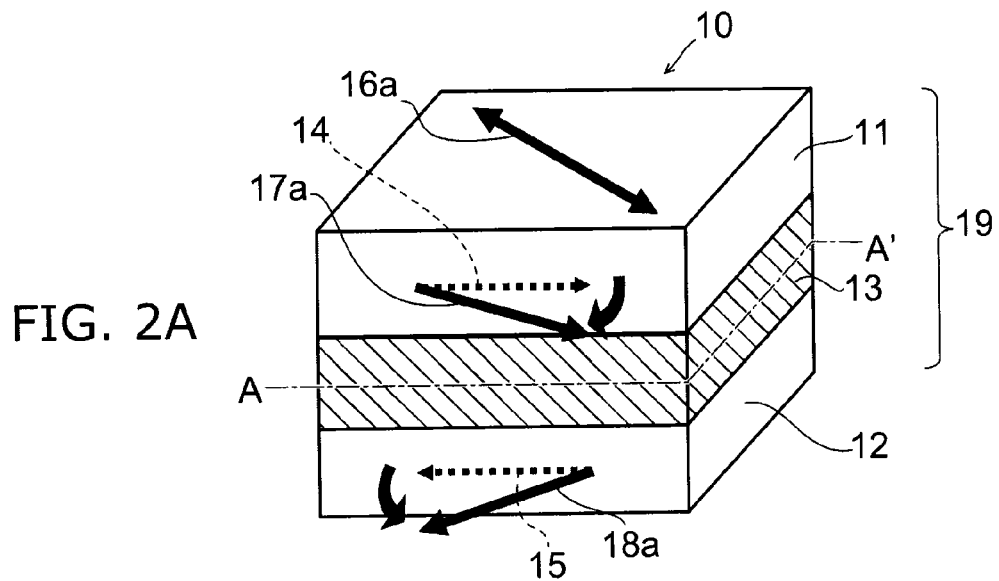
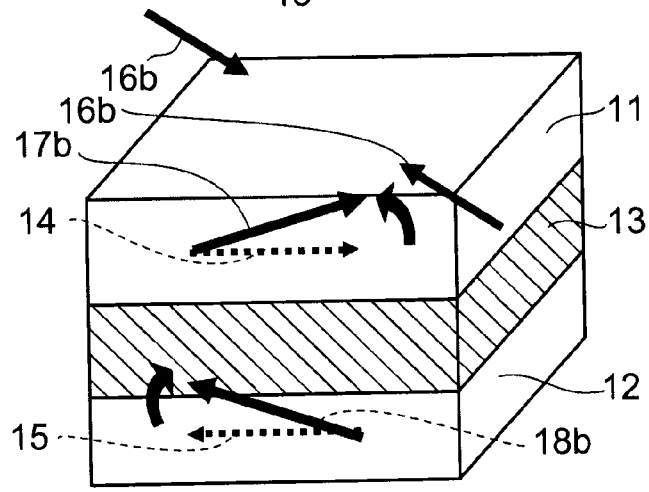
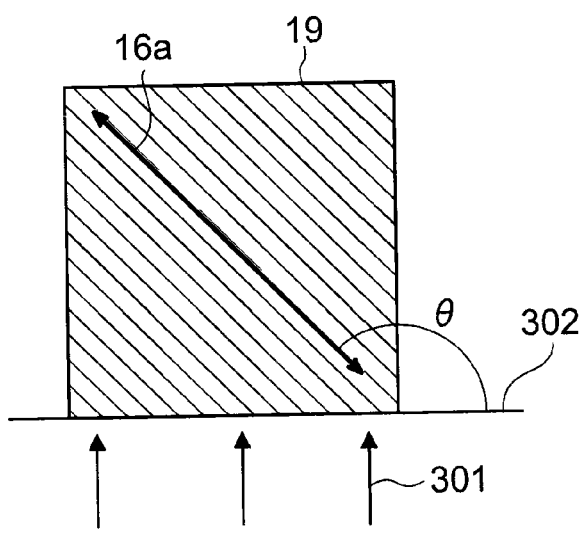
FIG. 2A
FIG. 2B
FIG. 2C

MAGNETO-RESISTIVE EFFECT DEVICE, MAGNETIC HEAD GIMBAL ASSEMBLY, MAGNETIC RECORDING/REPRODUCTION DEVICE, STRAIN SENSOR, PRESSURE SENSOR, BLOOD PRESSURE SENSOR, AND STRUCTURAL HEALTH MONITORING SENSOR

CROSS-REFERENCE TO RELATED APPLICATIONS

This application is a division of and claims the benefit of priority under 35 U.S.C. §120 from U.S. Ser. No. 13/246,069 filed Sep. 27, 2011, and claims the benefit of priority under 35 U.S.C. §119 from Japanese Patent Application No. 2011-066017 filed Mar. 24, 2011; the entire contents of which are incorporated herein by reference.

FIELD

Embodiments described herein relate generally to a magneto-resistive effect device, a magnetic head gimbal assembly, a magnetic recording/reproduction device, a strain sensor, a pressure sensor, a blood pressure sensor, and a structural health monitoring sensor.

BACKGROUND

The performance of magnetic devices using a stacked structure of magnetic material layers, in particular the performance of magnetic heads, has dramatically improved. In particular, in the technical field of magnetic heads using spin-valve films (Spin-Valve: SV film) there has been great progress.

A "spin-valve film" is a stacked film in which a nonmagnetic layer is sandwiched between two ferromagnetic layers, and one ferromagnetic layer (referred to as a "pinned layer") is a layer whose magnetization direction is pinned by an antiferromagnetic layer, and the other ferromagnetic layer is a layer whose magnetization can respond to external magnetic fields (referred to as a "free layer").

The spin-valve film functions as a type of variable resistance device. The resistance of carriers that move through the spin-valve film depends on the carrier spin state. Therefore, by changing the spin state of the spin-valve film with an external magnetic field, it is possible to change the resistance state of the spin-valve film.

The magneto-resistance effect (the MR effect) in which electrical resistance is varied by an external magnetic field gives rise to many physical phenomena. The most well-known are giant magnetoresistance (GMR) and tunneling magnetoresistance (TMR).

The electrical resistance state of a magneto-resistive effect device that includes a spin-valve film is determined by adjacent ferromagnetic layers, for example by the relative relationship between magnetization directions of the pinned layer and the free layer. Typically, in a spin-valve film, when the magnetization directions of the two ferromagnetic layers are aligned parallel, the electrical resistance state is in the "low resistance state". This state is conventionally represented as the "0" state. On the other hand, when the magnetization directions of the two ferromagnetic layers are aligned antiparallel, the electrical resistance state is in the "high resistance state". This state is conventionally represented as the "1" state. When the angle between the magnetization directions of the adjacent layers is an intermediate angle, the resistance state is intermediate. A magneto-resistive effect device that uses this phenomenon is widely used in reading heads for HDDs.

A magneto-resistive effect device with two free layers and that does not have a pinned layer and a pinning layer is being investigated as a head suitable for narrow gaps that are suitable for high densification, in contrast to magneto-resistive effect devices having a conventional pinned layer. In this structure, top and bottom magnetic layers with a spacer layer disposed therebetween both function as free layers. However, when the two free layers are oriented in the same magnetization direction, they do not function as a magnetic field sensor, so it is necessary that there be some measure to bias the two magnetic layers in different directions. This cannot be achieved with a bias using just a conventional hard bias layer, but an extremely complex bias is necessary. Therefore, at present the magneto-resistive effect device with two free layers has not reached the stage of practical use.

On the other hand, strain sensors that use the MR effect have been proposed, and a strain sensor using the MR effect has an area smaller than a conventional strain sensor, and can achieve extremely high sensitivity.

However, in a strain sensor that includes a conventional pinned layer, a spacer layer, and a free layer, there is only one free layer which operates magnetically as a unit (if a free layer is formed in a stacked film, and if there is rotation of magnetization as a unit magnetically, it becomes a single free layer). In this case, if the free layer uses the inverse magnetostrictive effect to detect strain, the magnetostriction coefficient of the free layer is either positive or negative only, so meaningful magnetization rotation only occurs for one of compressive stresses or tensile stresses, so the strain sensor is only capable of detecting one type of strain state. In this case there is the problem that when it is necessary to detect the strain at many points, the total sensitivity is reduced. A strain sensor that is capable of detecting either compressive stresses or tensile stresses is necessary.

BRIEF DESCRIPTION OF THE DRAWINGS

FIGS. 2A through 2C illustrate changes in magnetization direction when a strain is applied to the magnetic layers having positive and negative magnetostriction coefficients in the magneto-resistive effect device according to the first embodiment, FIG. 2A illustrates a tensile strain, FIG. 2B illustrates a compressive strain, and FIG. 2C is a cross-sectional view of the plane A-A' indicated in FIG. 2A;

FIG. 4A illustrates a case where there is no external magnetic field, FIG. 4B illustrates a case where an external magnetic field is directed away from the device, and FIG. 4C illustrates a case where an external magnetic field is directed towards the device;

FIG. 5A illustrates a case where there is no external magnetic field, FIG. 5B illustrates a case where an external magnetic field is directed away from the device, and FIG. 5C illustrates a case where an external magnetic field is directed towards the device;

FIG. 18A illustrates a case in which a tensile strain is applied, and FIG. 18B illustrates a case in which a compressive strain is applied;

FIG. 19A illustrates a case in which a tensile strain is applied in an arbitrary direction, FIG. 19B illustrates a case in which a compressive strain is applied in an arbitrary direction, and FIG. 19C illustrates a case in which a compressive strain is applied and prior to application of the strain the magnetization directions of the two ferromagnetic layers are antiparallel;

FIG. 22A illustrates a case where a compressive strain is applied to the device A, FIG. 22B illustrates a case where a tensile strain is applied to the device A, FIG. 22C illustrates a case where a compressive strain is applied to the device B, and FIG. 22D illustrates a case where a tensile strain is applied to the device B;

FIG. 26A illustrates a case of application of a tensile strain, and FIG. 26B illustrates a case of application of a compressive strain;

DETAILED DESCRIPTION

Figure 1:
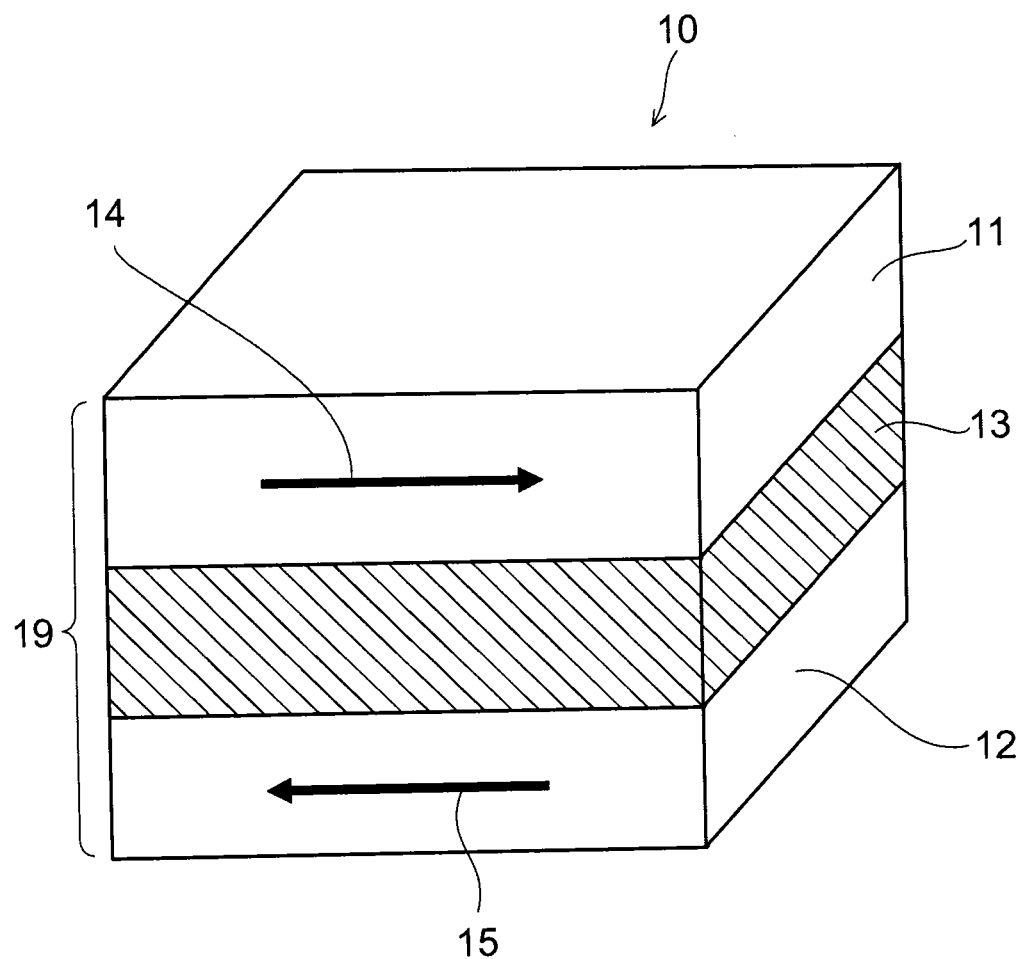
FIG. 1 is a perspective view illustrating a magneto-resistive effect device according to a first embodiment.

In general, according to one embodiment, a magneto-resistive effect device, includes a stacked body stacked on a substrate, a pair of first electrodes that feeds current to the stacked body, a strain introduction member, and a second electrode for applying a voltage to the strain introduction member. The stacked body includes a first magnetic layer that includes one or more metals selected from the group consisting of iron, cobalt, and nickel, a second magnetic layer stacked on the first magnetic layer, having a composition that is different from the first magnetic layer, and a spacer layer disposed between the first magnetic layer and the second magnetic layer. The strain introduction member applies strain to the stacked body. The strain introduction member is provided near the stacked body. By applying strain to the stacked body, the strain introduction member biases magnetization directions of the first magnetic layer and the second magnetic layer in different directions. The magnetization directions of the first magnetic layer and the second magnetic layer are changed by the application of an external magnetic field. The external magnetic field is detected by a change in resistance between the first electrodes due to the change in the magnetization directions.

According to another embodiment, a magnetic head gimbal assembly includes a magneto-resistive effect device. a magneto-resistive effect device, includes a stacked body stacked on a substrate, a pair of first electrodes that feeds current to the stacked body, a strain introduction member, and a second electrode for applying a voltage to the strain introduction member. The stacked body includes a first magnetic layer that includes one or more metals selected from the group consisting of iron, cobalt, and nickel, a second magnetic layer stacked on the first magnetic layer, having a composition that is different from the first magnetic layer, and a spacer layer disposed between the first magnetic layer and the second magnetic layer. The strain introduction member applies strain to the stacked body. The strain introduction member is provided near the stacked body. By applying strain to the stacked body, the strain introduction member biases magnetization directions of the first magnetic layer and the second magnetic layer in different directions. The magnetization directions of the first magnetic layer and the second magnetic layer are changed by the application of an external magnetic field. The external magnetic field is detected by a change in resistance between the first electrodes due to the change in the magnetization directions.

According to another embodiment, a magnetic recording/reproduction device includes a magnetic head gimbal assembly that includes a magneto-resistive effect device, a magnetic head that includes the magneto-resistive effect device, mounted on the magnetic head gimbal assembly, and a magnetic recording medium that reproduces information using the magnetic head. The magneto-resistive effect device includes a stacked body stacked on a substrate, a pair of first electrodes that feeds current to the stacked body, a strain introduction member, and a second electrode for applying a voltage to the strain introduction member. The stacked body includes a first magnetic layer that includes one or more metals selected from the group consisting of iron, cobalt, and nickel, a second magnetic layer stacked on the first magnetic layer, having a composition that is different from the first magnetic layer, and a spacer layer disposed between the first magnetic layer and the second magnetic layer. The strain introduction member applies strain to the stacked body. The strain introduction member is provided near the stacked body. By applying strain to the stacked body, the strain introduction member biases magnetization directions of the first magnetic layer and the second magnetic layer in different directions. The magnetization directions of the first magnetic layer and the second magnetic layer are changed by the application of an external magnetic field. The external magnetic field is detected by a change in resistance between the first electrodes due to the change in the magnetization directions.

According to another embodiment, a strain sensor includes a substrate, a stacked body fixed to the substrate, and a pair of electrodes that feeds current to the stacked body. The stacked body includes a first magnetic layer that includes one or more metals selected from the group consisting of iron, cobalt, and nickel, a second magnetic layer stacked on the first magnetic layer, having a composition that is different from the first magnetic layer, and a spacer layer disposed between the first magnetic layer and the second magnetic layer. The magnetization of both the first magnetic layer and the second magnetic layer rotates due to external strain applied to the stacked body. The external strain is detected by a change in the resistance between the electrodes associated with the rotation of the magnetization of the first magnetic layer and the second magnetic layer.

According to another embodiment, a pressure sensor includes a strain sensor. The strain sensor includes a substrate, the stacked body fixed to the substrate, and a pair of electrodes that feeds current to the stacked body. The substrate includes a flexible membrane to which a stacked body is fixed and a support part that supports the membrane. The stacked body includes a first magnetic layer that includes one or more metals selected from the group consisting of iron, cobalt, and nickel, a second magnetic layer stacked on the first magnetic layer, having a composition that is different from the first magnetic layer, and a spacer layer disposed between the first magnetic layer and the second magnetic layer. The magnetization of both the first magnetic layer and the second magnetic layer rotates due to external strain applied to the stacked body. The external strain is detected by a change in the resistance between the electrodes associated with the rotation of the magnetization of the first magnetic layer and the second magnetic layer. External pressure is detected by detecting strain on the membrane due to external pressure.

According to another embodiment, a blood pressure sensor that monitors the blood pressure of a person or an animal includes a strain sensor. The strain sensor includes a substrate, a stacked body fixed to the substrate, and a pair of electrodes that feeds current to the stacked body. The stacked body includes a first magnetic layer that includes one or more metals selected from the group consisting of iron, cobalt, and nickel, a second magnetic layer stacked on the first magnetic layer, having a composition that is different from the first magnetic layer, and a spacer layer disposed between the first magnetic layer and the second magnetic layer. The magnetization of both the first magnetic layer and the second magnetic layer rotates due to external strain applied to the stacked body. External strain is detected by a change in the resistance between the electrodes associated with the rotation of the magnetization of the first magnetic layer and the second magnetic layer.

According to another embodiment, a structural health monitoring sensor that performs structural condition monitoring to monitor a strain state of a bridge or building structure include a strain sensor. The strain sensor includes a substrate, a stacked body fixed to the substrate, the stacked body, and a pair of electrodes that pass current through the stacked body. The stacked body includes a first magnetic layer that includes one or more metals selected from the group consisting of iron, cobalt, and nickel, a second magnetic layer stacked on the first magnetic layer, having a composition that is different from the first magnetic layer, and a spacer layer disposed between the first magnetic layer and the second magnetic layer. The magnetization of both the first magnetic layer and the second magnetic layer rotate due to external strain applied to the stacked body. External strain is detected by a change in the resistance between the electrodes associated with the rotation of the magnetization of the first magnetic layer and the second magnetic layer.

Various embodiments will be described hereinafter with reference to the accompanying drawings.

First Embodiment

Hereinafter, embodiments of the invention will be explained below with reference to the drawings.

First, a first embodiment will be described.

FIG. 1 is a perspective view illustrating the magneto-resistive effect device according to the first embodiment.

As illustrated in FIG. 1, a magneto-resistive effect device 10 has a stacked structure that includes a ferromagnetic layer 12 whose magnetization direction can be rotated by an external magnetic field, and a ferromagnetic layer 11 stacked on the ferromagnetic layer 12 and whose magnetization direction can be rotated by an external magnetic field. In this embodiment, a spacer layer 13 is provided between the ferromagnetic layer 11 and the ferromagnetic layer 12. The ferromagnetic layer 11 and the ferromagnetic layer 12 are made from materials that exhibit the inverse magnetostrictive effect. However, the polarities of the inverse magnetostrictive effect of the ferromagnetic layer 11 and the ferromagnetic layer 12 are mutually opposite. For example, the ferromagnetic layer 11 has a positive magnetostriction coefficient, and the ferromagnetic layer 12 has a negative magnetostriction coefficient.

In the following, the stacked body in which the ferromagnetic layer 11, the spacer layer 13, and the ferromagnetic layer 12 are stacked is referred to as a "stacked body 19", the direction in which the ferromagnetic layer 11, the spacer layer 13, and the ferromagnetic layer 12 are stacked is referred to as the "stacking layer", and any direction normal to the stacking direction is referred to as the "in-plane direction".

The following are specific examples of materials with different magnetization polarity of the ferromagnetic layer 11 and the ferromagnetic layer 12 of the magneto-resistive effect device.

The magnetic layer that has a positive magnetostriction coefficient includes one or more metals selected from the group consisting of iron, cobalt, and nickel.

On the other hand, the magnetic layer that has a negative magnetostriction coefficient includes basically one or more metals selected from the group consisting of iron, cobalt, and nickel. Of these, the use of a material that includes one or more of the metals selected from the group consisting of nickel and samarium iron (SmFe) is suitable. In the case of a metal spacer layer, a CoFe alloy layer is suitable as a material that has negative magnetostriction.

In the following, as an example, the stacked body 19 that includes a magnetic layer having a positive magnetostriction coefficient, a spacer layer, and a magnetic layer having a negative magnetostriction coefficient is described.

Normally, the magnetostriction of a magnetic layer is determined by the composition of the magnetic layer. The general trends of these compositions have been investigated in many publications to date. However, a characteristic situation that occurs with very thin films is that the actual magnetostriction is greatly affected by the material adjacent to a magnetic layer.

If an oxide material is used as the spacer layer 13 (a tunnel barrier layer such as magnesium oxide (MgO) or a CCP layer that is described later), when a magnetic layer that includes cobalt iron (CoFe) or the like is used at an interface with the spacer layer 13, the magnetic layers normally have positive magnetostriction within 1 to 2 nm of the top and bottom surfaces of spacer layer 13. This is because oxide layers such as $CoFeBO_x$, $CoO_x$, $NiO_x$, and $FeO_x$, and so on are materials that have positive magnetostriction. Next, in this embodiment, a constitution that exhibits different positive and negative magnetostriction is formed using the ferromagnetic layers 11 and 12. The interface of the oxide layer already exhibits positive magnetostriction, so it is comparatively easy to form a magnetic layer with positive magnetostriction as either the whole free layer 11 or the whole free layer 12. Therefore, at the other interface, in order to form negative magnetostriction, by stacking a magnetic layer with large negative magnetostriction onto the oxide interfacial layer that has positive magnetostriction, the magnetic layer with negative magnetostriction can be formed as the total free layer 11 or the free layer 12. Large negative magnetostriction can be achieved using a nickel (Ni) rich alloy.

Other examples for forming negative magnetostriction include, for example, nickel (Ni), NiFe alloy (including not less than 85 at % Ni), SmFe, and so on. If magnetic material is formed from in a plurality of layers, it forms a magnetic layer with a magnetization direction acting magnetically as a unit. The magnetostriction of the magnetic layers is determined by the total stacked film constitution of the magnetic layers (on the other hand, the other magnetic layer with the nonmagnetic layer disposed therebetween functions as a separate magnetic layer, so the magnetostriction is defined as a separate value.

A specific example of the stacked film constitution of the ferromagnetic layer 11/spacer layer 13/ferromagnetic layer 12 is a stacked film of $Co_{90}Fe_{10}$/CoFeB/MgO/CoFeB/$Ni_{95}Fe_5$, with film thicknesses of 2 nm/1 nm/1.5 nm/1 nm/2 nm respectively. Here, the $Co_{90}Fe_{10}$/CoFeB layers function as a single magnetic layer that exhibits positive magnetostriction, and the CoFeB/$Ni_{95}Fe_5$ layers function as a single magnetic layer that exhibits negative magnetostriction. The MgO layer is the spacer layer.

There are various types of spacer layer depending on the physical mechanism of the magnetoresistance.

When using the GMR effect of a current in plane (CIP) structure or a current perpendicular to the plane (CPP) structure, a nonmagnetic metal is used as the material of the spacer layer. Also, the nonmagnetic metal may be one metal selected from the group consisting of copper, gold, silver, aluminum, and chromium.

Here, a CIP structure is a structure in which a pair of electrodes is provided at two ends in the in-plane direction of the stacked body of the ferromagnetic layer 11 and the ferromagnetic layer 12, and the pair of electrodes feeds current to the stacked body in the in-plane direction. Also, a CPP structure is a structure in which a pair of electrodes is provided at the two ends in the stacking direction of the stacked body of the ferromagnetic layer 11 and the ferromagnetic layer 12, and current flows through the stacked body in the stacking direction.

The spacer layer is also used in a current configured path (CCP) structure, which does not have a uniform metal layer. The spacer layer in a CCP structure is an insulating layer with a film thickness in the order of nanometers, with electrically conducting material embedded in through holes. The advantage of a spacer layer with a CCP structure is that the MR effect is increased, while maintaining a low resistance. The material of the electrically conducting material in a spacer layer with a CCP structure is one metal selected from the group consisting of copper, gold, silver, aluminum, and chromium. The material of the insulating material of a spacer layer with a CCP structure is an oxide or nitride of one type of metal selected from the group consisting of aluminum, titanium, zinc, silicon, hafnium, tantalum, molybdenum, tungsten, niobium, chromium, magnesium, and zirconium.

If TMR is used, the spacer layer 13 is formed from a typical insulating material such as magnesium oxide, in order to obtain high electrical resistance. A spacer layer made from such an insulating material functions as a tunnel barrier layer. Here, tunnel barrier layer refers to an insulating layer through which current can flow as a result of the tunnel effect. Besides magnesium oxide as described above, magnesium nitride, or an oxide or nitride of one metal selected from the group consisting of aluminum, titanium, zinc, silicon, hafnium, tantalum, molybdenum, tungsten, niobium, chromium, and zirconium can be used as the material of the tunnel barrier layer.

As stated above, of the two ferromagnetic layers included in the magneto-resistive effect device, one exhibits positive magnetostriction coefficient, and the other exhibits negative magnetostriction coefficient, with the spacer layer disposed therebetween. For example, in the process of forming the films to form the stacked body 19 illustrated in FIG. 1, the layer with the positive magnetostriction coefficient, the spacer layer, and the layer with the negative magnetostriction coefficient may be formed in that order from the bottom up, or conversely the layer with the negative magnetostriction coefficient, the spacer layer, and the layer with the positive magnetostriction coefficient may be formed in that order from the bottom up.

In order to explain the operating principle of this embodiment as illustrated in FIG. 1, first the state in which the external strain is very small is illustrated. The initial magnetization directions 14 and 15 of the ferromagnetic layer 11 and the ferromagnetic layer 12 are antiparallel. This corresponds to a state of static magnetic coupling between the two magnetic layers, or a case in which the antiferromagnetic coupling component due to RKKY interaction is large, or the like. However, there is also the case where the initial magnetization directions of the first ferromagnetic layer 11 and the second ferromagnetic layer 12 are parallel such as when there is strong magnetic field coupling between the two ferromagnetic layers. In the following explanation, the principle is explained in substantially the same way whether the initial state is a parallel magnetization state or an antiparallel magnetization state.

Next, operation of the magneto-resistive effect device according to the first embodiment will be described.

First, the magnetostrictive effect is explained.

The magnetostrictive effect is the generation of a strain in a magnetic material by changing the magnetization direction of the magnetic material. The strain generated by the magnetostrictive effect depends on the magnitude and direction of magnetization. Therefore, the magnitude of the strain due to the magnetostrictive effect is controlled by the magnitude and direction of magnetization. Also, the magnitude of the strain due to the magnetostriction greatly depends on the characteristic magnetostriction coefficient of the magnetic material. The value of the ratio of the change in strain in the state where the magnetization is saturated is referred to as the magnetostriction coefficient.

There is also the inverse magnetostrictive effect, which is the opposite phenomenon of the magnetostrictive effect. The inverse magnetostrictive effect is the phenomenon in which the direction of magnetization of a magnetic material is changed by an externally applied strain. The magnitude of the change in magnetization direction in the inverse magnetostrictive effect depends on the magnitude of the externally applied strain and the characteristic magnetostriction coefficient of the magnetic material. The magnetostrictive effect and the inverse magnetostrictive effect are physically symmetrical, and the magnetostriction coefficient has the same value in both effects.

The magnetostriction coefficient in the magnetostrictive effect and the inverse magnetostrictive effect can be either a positive magnetostriction coefficient or a negative magnetostriction coefficient, depending on the magnetic material.

In the inverse magnetostrictive effect, in the case of a magnetic material with a positive magnetostriction coefficient, when a tensile strain is applied to the magnetic material, the direction of magnetization of the magnetic material is changes to a direction that coincides with the direction of the applied strain. It is this direction because this direction is energetically stable. Also, when a compressive strain is applied to the magnetic material, the direction of magnetization of the magnetic material changes to a direction that is normal to the direction of the applied strain.

On the other hand, in the case of a magnetic material with a negative magnetostriction coefficient, the opposite is the case. In other words, when a compressive strain is applied to the magnetic material, the magnetization direction of the magnetic material changes to a direction that coincides with the direction of the applied strain. On the other hand, when a tensile strain is applied, the direction of magnetization of the magnetic material changes to a direction that is normal to the direction of the applied strain.

In this way, in states in which strain with a single polarity is applied (in other words, only one of either compression or tension), the directions of magnetization of the two magnetic layers having different polarity magnetostriction coefficients change to different directions. By using this phenomenon it is possible to realize a bias structure with two free layers. In other words, it is possible to set the angle between the magnetization directions of the two magnetic layers to about 90 degrees.

FIGS. 2A through 2C illustrate the change in magnetization direction when a strain is applied to the magnetic layers having positive and negative magnetostriction coefficients in the magneto-resistive effect device according to the first embodiment, FIG. 2A illustrates a tensile strain, FIG. 2B illustrates a compressive strain, and FIG. 2C is a cross-sectional view of the plane A-A' indicated in FIG. 2A.

As illustrated in FIG. 2A, if a tensile strain 16a is applied to the magneto-resistive effect device 10, the magnetization direction 14 of the ferromagnetic layer 11 which has a positive magnetostriction coefficient changes so that the angle with the direction of the tensile strain 16a becomes smaller, in other words, rotates towards the direction of the tensile strain 16a to a magnetization direction 17a. Conversely, the magnetization direction 15 of the ferromagnetic layer 12 which has a negative magnetostriction coefficient changes so that the angle with the direction of the tensile strain 16a becomes larger, in other words, rotates towards a direction normal to the direction of the tensile strain 16a to a magnetization direction 18a.

On the other hand, if a compressive strain 16b is applied instead of the tensile strain 16a, the opposite occurs. In other words, as illustrated in FIG. 2B, the magnetization direction 14 of the ferromagnetic layer 11 which has a positive magnetostriction coefficient rotates towards a direction normal to the direction of the compressive strain 16b to a magnetization direction 17b. Conversely, the magnetization direction 15 of the ferromagnetic layer 12 which has a negative magnetostriction coefficient rotates towards the direction of the compressive strain 16b to a magnetization direction 18b.

In this way, regardless of the polarity of the strain, such as tensile strain or compressive strain, and even if a single polarity strain is applied, the magnetization directions of the two magnetic layers which have positive and negative magnetostriction coefficients are induced to approach a right angle to each other. Therefore, the application of strain can be used to bias the magnetization directions of the two free layers in different directions.

Next, the effect of the magneto-resistive effect device according to the first embodiment will be described.

As stated previously, in a magneto-resistive effect device that includes two free layers, a bias structure to orient the magnetization directions of the two magnetic layers in different directions was extremely difficult.

However, by using materials with different magnetostriction polarity in the two ferromagnetic layers with the spacer layer disposed therebetween, as in this embodiment, and applying an external strain with a single polarity to the stacked film, it is possible to achieve an appropriate bias with respect to the magnetization directions of the two magnetic layers. In other words, it is possible to realize a magneto-resistive effect device with thin film thickness that does not have a pinned layer and a pinning layer. In this way it is possible to realize a magneto-resistive effect device suitable for high densification and suitable for narrow gaps.

Second Embodiment

Next a second embodiment will be described.

This embodiment is an embodiment of a magnetic head.

The magnetic head according to this embodiment is provided with the magneto-resistive effect device according to the first embodiment.

Figure 3:
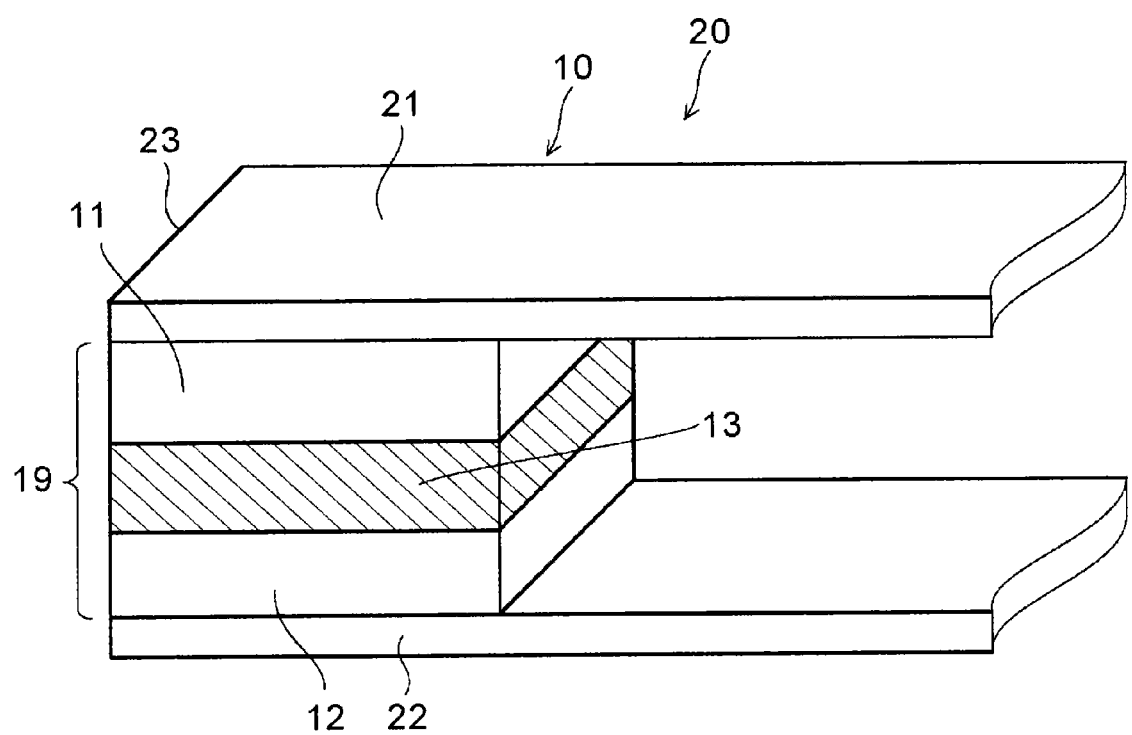
FIG. 3 is a perspective view illustrating a magnetic head according to a second embodiment.

FIG. 3 is a perspective view illustrating the magnetic head according to the second embodiment.

As illustrated in FIG. 3, a magnetic head 20 is provided with the stacked body 19 that constitutes the magneto-resistive effect device 10, and, if the stacking direction is the vertical direction, with a top electrode 21 on the top surface thereof, and a bottom electrode 22 on the bottom surface thereof.

As illustrated in FIG. 3, one side surface of the four side surfaces of the stacked body 19 is taken to be an ABS surface 23. In the ABS surface 23, both the top electrode 21 and the bottom electrode 22 are exposed. In other words, an end edge of the top electrode 21 and an end edge of the bottom electrode 22 form part of the ABS surface 23. In this embodiment, an example in which the magneto-resistive effect device 10 is applied to a magnetic head that measures external magnetic fields, for example the magnetic field from magnetic media, is explained. The ABS surface 23 is disposed facing a rotating magnetic medium. In this way, the magnetization directions of the two magnetic layers of the stacked body 19 are changed by the magnetic flux generated by the magnetic medium.

In this embodiment, strain can be introduced to the magneto-resistive effect device 10 by using stress generated during manufacture of the magnetic head 20, but the strain can also be actively introduced by various means.

In the process of producing a magnetic head, after forming the devices at wafer level, a lapping process is carried out that mechanically grinds the film cross-section of the magneto-resistive effect device. The orientation of this lapping is applied from one cross-section, so a stress with a single polarity is applied to the magneto-resistive effect device. This stress can be used as a source of externally applied strain. In other words, the strain generated by grinding from the film cross-section of the stacked body can be used as the strain applied to the stacked body.

Also, while manufacturing the magneto-resistive effect device 10, strain can be introduced by a lattice mismatch between the layers of the stacked body 19. In addition, strain can be introduced by generating internal stress between the layers of the stacked body 19 by differences in thermal expansion. It is considered that the most controlled state is that due to an external stress. By using an external stress, it is possible to apply stress in the necessary part of the magneto-resistive effect device 10, and this is desirable state from the point of view of controllability.

The configuration of the magnetic head according to this embodiment has a current-perpendicular-to-plane (CPP) structure in which a sense current flows in a direction perpendicular to the film face of the stacked body 19. However, a current-in-plane (CIP) structure may be used in which electrodes are disposed on side surfaces of the stacked body 19, for example, the side surfaces apart from the ABS surface 23 and the opposite surface thereto, and sense current flows in the in-plane direction along the stacking surfaces.

Next, operation of the magnetic head according to the second embodiment will be described.

Figure 4A:
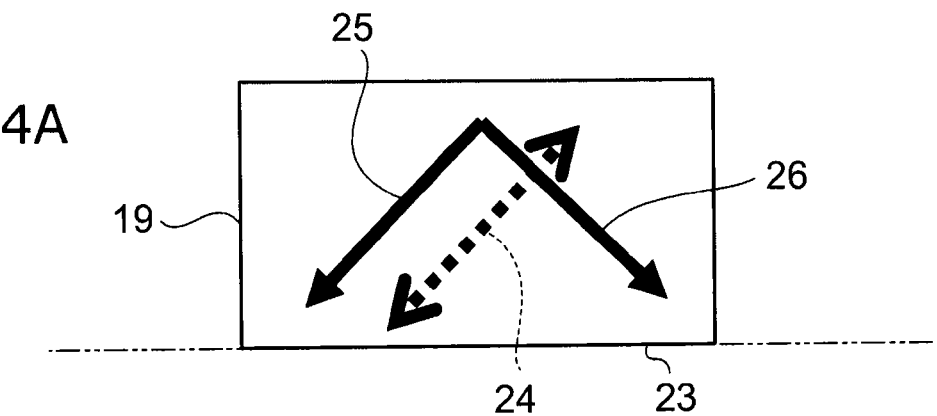
FIGS. 4A through 4C illustrate magnetization directions of the magneto-resistive effect device.
Figure 4B:
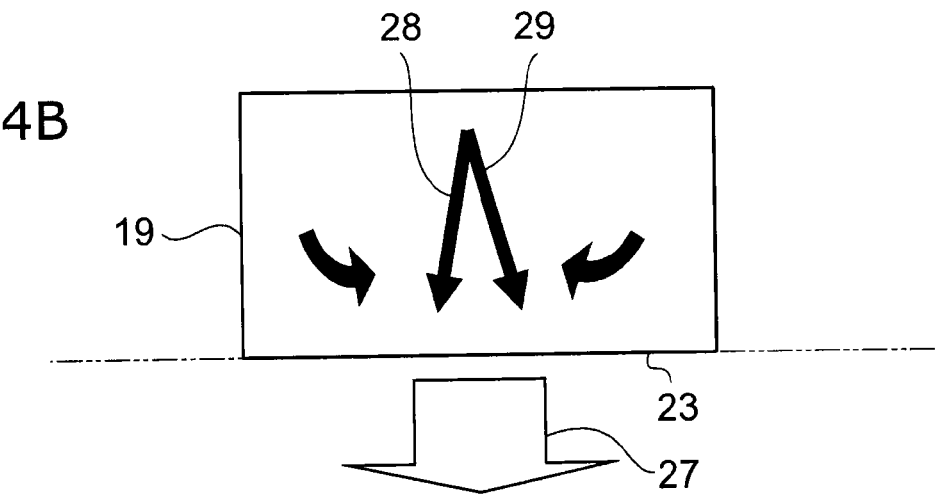
Figure 4C:
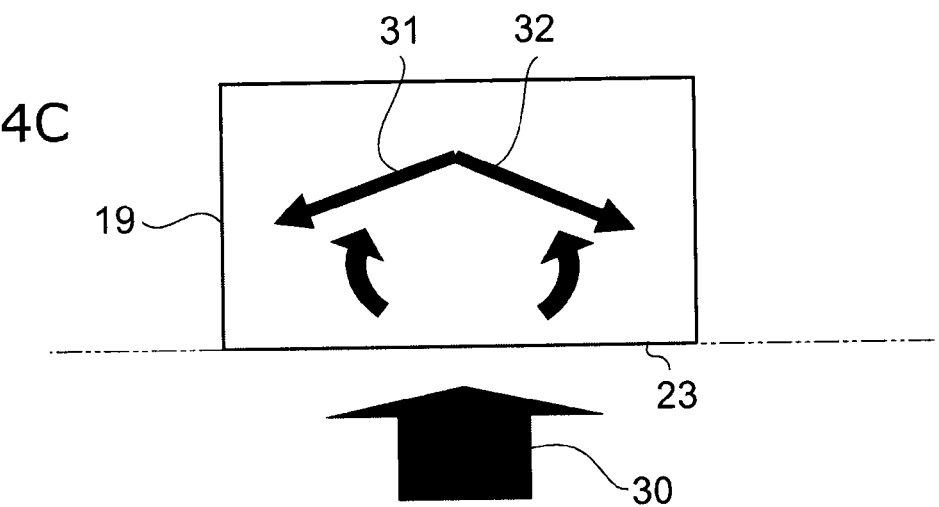

FIGS. 4A through 4C illustrate the magnetization directions of the magneto-resistive effect device, FIG. 4A illustrates a case where there is no external magnetic field, FIG. 4B illustrates a case where an external magnetic field is directed away from the device, and FIG. 4C illustrates a case where an external magnetic field is directed towards the device.

As illustrated in FIG. 4A, a tensile strain 24 is applied to the stacked body 19 of the magneto-resistive effect device 10 of the magnetic head 20, in a direction 45° from the ABS surface 23 when viewed from the top surface of the stacked body 19. An external magnetic field is applied from a direction normal to the ABS surface 23. Therefore, the tensile strain 24 is applied from a direction of 45° or 135° when viewed from the direction that the external magnetic field is applied. As stated above, the ferromagnetic layer 11 has a positive magnetostriction coefficient, and the ferromagnetic layer 12 has a negative magnetostriction coefficient.

First a case in which there is no magnetic field due to an external magnetic field is explained. The magnetization direction of the ferromagnetic layer 11 is a magnetization direction 25 along the direction of the tensile strain 24 at −135° from the ABS surface 23, when viewed from the top surface of the stacked body 19. With the ABS surface 23 as reference, counterclockwise is the rotation direction that increases the angle, and with the ABS surface 23 as reference, clockwise is the rotation direction that reduces the angle. On the other hand, the magnetization direction of the ferromagnetic layer 12 is a magnetization direction 26 that is normal to the direction of the tensile strain 24, at −45° from the ABS surface 23. In this case, the magnetization directions 25 and 26 of the two magnetic layers are mutually orthogonal. Therefore, the resistance state of the magneto-resistive effect device 10 is the intermediate state, as a result the operation of a normal spin-valve film. In this embodiment, a case in which a tensile strain is applied is described, but a compressive strain may also be applied.

Next, a case where an external magnetic field is applied is explained.

As illustrated in FIG. 4B, when an external magnetic field 27 due to an external magnetic flux is applied in a direction away from the device, in other words in a direction 27 at −90° from the ABS surface 23, when viewed from the top surface of the stacked body 19, the magnetization directions of the two magnetic layers rotate to approach the direction 27 of the external magnetic field. Therefore, the magnetization directions of the two magnetic layers become magnetization directions 28 and 29. As a result, the magnetization directions of the two magnetic layers approach parallel. In this way, the resistance state of the magneto-resistive effect device 10 is changed to approach the low resistance state.

In contrast, as illustrated in FIG. 4C, when an external magnetic field 30 due to an external magnetic flux is applied in a direction 30 towards the device, in other words in a direction 30 at 90° from the ABS surface 23, when viewed from the top surface of the stacked body 19, the magnetization directions of the two magnetic layers are rotated by the external magnetic field 30 to approach, and become magnetization directions 31 and 32. As a result, they tend to be aligned antiparallel. In this way, the resistance state of the magneto-resistive effect device 10 is changed to approach the high resistance state.

In FIGS. 4A through 4C, the magnitudes of the normal component and the horizontal component of the magnetization directions of the two magnetic layers of the magneto-resistive effect device 10 with respect to the ABS surface 23 were equal.

Next, a case will be explained in which the magnitudes of the normal component and the horizontal component of the magnetization directions of the two magnetic layers of the magneto-resistive effect device 10 with respect to the ABS surface 23 are different.

Figure 5A:
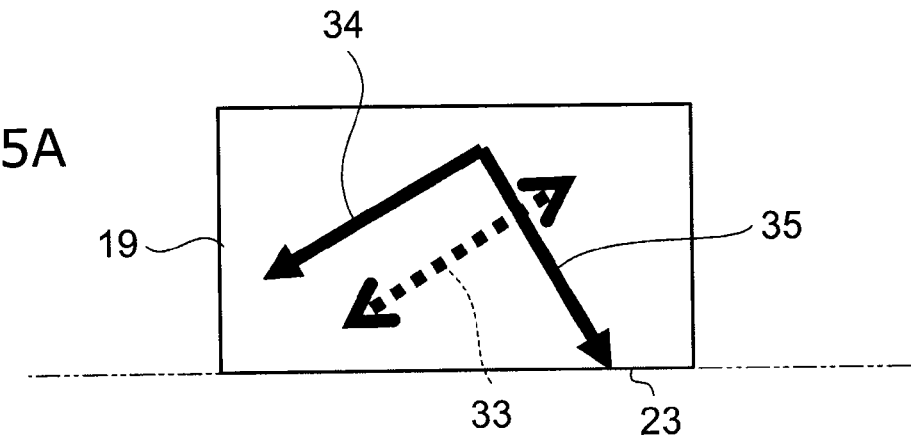
FIGS. 5A through 5C illustrate the magnetization directions of the magneto-resistive effect device.
Figure 5B:
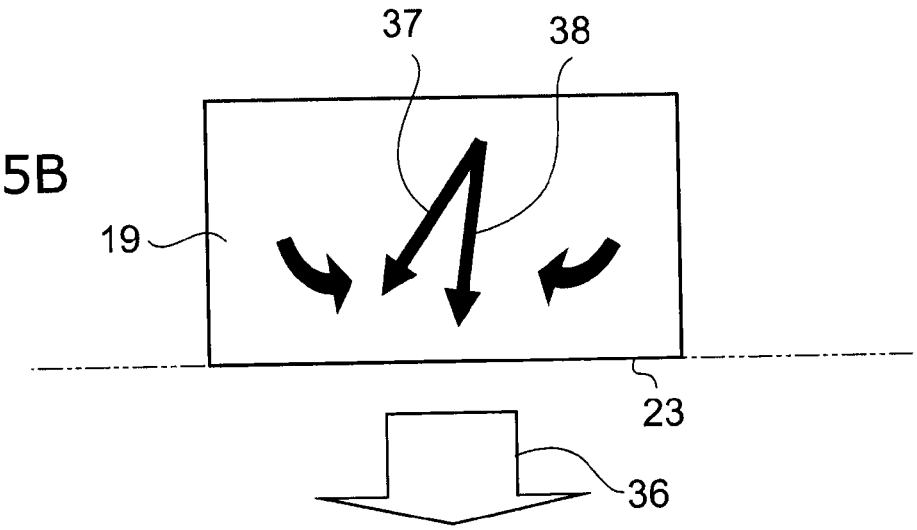
Figure 5C:
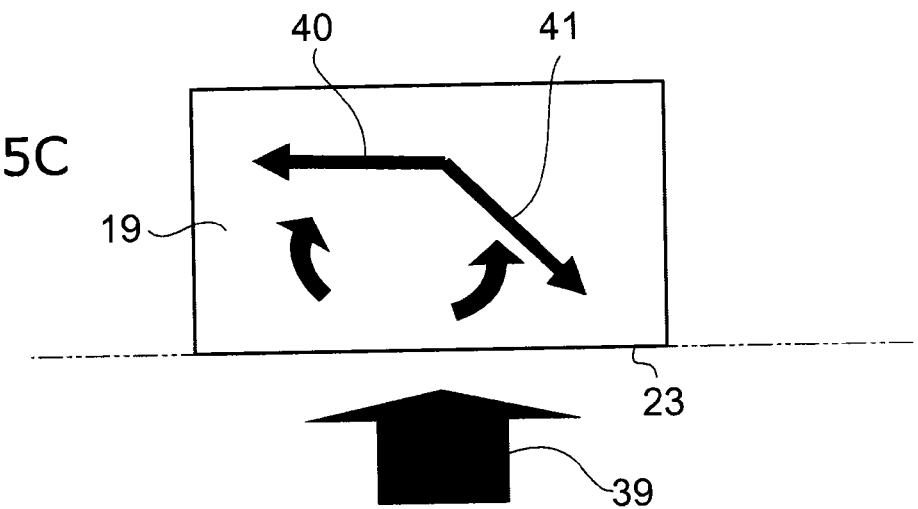

FIGS. 5A through 5C illustrate the magnetization directions of the magneto-resistive effect device, FIG. 5A illustrates a case where there is no external magnetic field, FIG. 5B illustrates a case where an external magnetic field is directed away from the device, and FIG. 5C illustrates a case where an external magnetic field is directed towards the device.

In the examples illustrated in FIGS. 5A through 5C, the ferromagnetic layer 11 has a positive magnetostriction coefficient, and the ferromagnetic layer 12 has a negative magnetostriction coefficient.

As illustrated in FIG. 5A, a tensile strain 33 is applied to the stacked body 19 of the magneto-resistive effect device 10 of the magnetic head 20, in a direction between 0 to 45° from the ABS surface 23 when viewed from the top surface of the stacked body 19. First a case in which there is no magnetic field due to an external magnetic flux is explained. The magnetization direction of the ferromagnetic layer 11 is rotated along the direction of the tensile strain 33, in a direction 34 between −135 to −180° from the ABS surface 23, when viewed from the top surface of the stacked body 19. On the other hand, the magnetization direction of the ferromagnetic layer 12 is rotated normal to the direction of the tensile strain 33, in a direction between −45 to −90° from the ABS surface 23. In this case, the magnetization directions 34 and 35 of the two ferromagnetic layers are orthogonal. Therefore, the resistance state of the magneto-resistive effect device is the intermediate state, as a result of the operation of a normal spin-valve film.

Next, a case where an external magnetic field is applied is explained.

As illustrated in FIG. 5B, when an external magnetic field 36 due to an external magnetic flux is applied in a direction away from the device 10, in other words in a direction at −90° from the ABS surface 23, when viewed from the top surface of the stacked body 19, the magnetization directions of the two ferromagnetic layers rotate to approach closer to the external magnetic field 36, becoming the magnetization directions 37 and 38. As a result, they tend to be aligned closer to parallel. In this way, the resistance state approaches the low resistance state. In contrast, as illustrated in FIG. 5C, when an external magnetic field 39 due to an external magnetic flux is applied in a direction towards the device, in other words in a direction 90° from the ABS surface 23, when viewed from the top surface of the stacked body 19, the magnetization directions of the two magnetic layers are rotated by the external magnetic field 39 to approach closer, and become magnetization directions 40 and 41. As a result, they tend to be aligned closer to antiparallel. In this way, the resistance state approaches the high resistance state.

As explained above, as long as the magnetization directions of the two ferromagnetic layers have components normal to the direction of an external magnetic field, it is possible to detect the external magnetic field by the changes in the resistance state by the spin-valve film. Also, in order that both the magnetization directions of the two ferromagnetic layers have a component normal to the direction of the external magnetic field, the magnetization directions of the two ferromagnetic layers may be configured so as to intersect. Then, the two ferromagnetic layers in this embodiment have positive and negative magnetostriction coefficients, so if a strain in a direction normal to the stacking direction of the stacked body is introduced into the stacked body, the magnetization directions of the two ferromagnetic layers intersect. Hence it is possible to detect external magnetic fields.

In other words, setting the angle θ between the magnetization of the two ferromagnetic layers with the spacer layer disposed therebetween to approximately 90 degrees is the most preferable state for stability of operation of the device. At least, it is necessary that the angle θ be set in the range 0 degrees<θ<180 degrees.

Next, a case in which an external magnetic field is continuously changing between the external magnetic field 27 whose direction is away from the device and the external magnetic field 30 whose direction is towards the device is explained, as an example of reading a magnetic medium.

First, the tensile strain 24 as illustrated in FIG. 4A is introduced, with the magnetization directions of the two ferromagnetic layers intersecting as in the magnetization directions 25 and 26. Then, a sense current is passed between electrodes 21 and 22. As stated above, the resistance state is detected to be the intermediate resistance state.

Then, as the magnetic medium moves, if the resistance becomes lower, as illustrated in FIG. 4B, it is determined that the magnetization directions of the two ferromagnetic layers have approached parallel. Therefore, "1" is read as the external magnetic field 27 recorded on the magnetic medium below the ABS surface 23 of the magnetic head.

On the other hand, as the magnetic medium moves, if the resistance becomes high, as illustrated in FIG. 4C, it is determined that the magnetization directions of the two ferromagnetic layers have approached antiparallel. Therefore, "0" is read as the external magnetic field 30 recorded on the magnetic medium below the ABS surface 23 of the magnetic head.

Next, the effect of the magnetic head according to the second embodiment will be described.

In the magnetic head according to the second embodiment, the ferromagnetic layer with the positive magnetostriction coefficient and the ferromagnetic layer with the negative magnetostriction coefficient are stacked with the spacer layer disposed therebetween, in addition, by applying a strain to the stacked body 19, it is possible to apply a bias in different directions to the two free layers, so it is possible to detect external magnetic fields. Therefore, it is possible to realize a magnetic head suitable for high densification.

Third Embodiment

Next, a magnetic head according to a third embodiment will be described.

Figure 6:
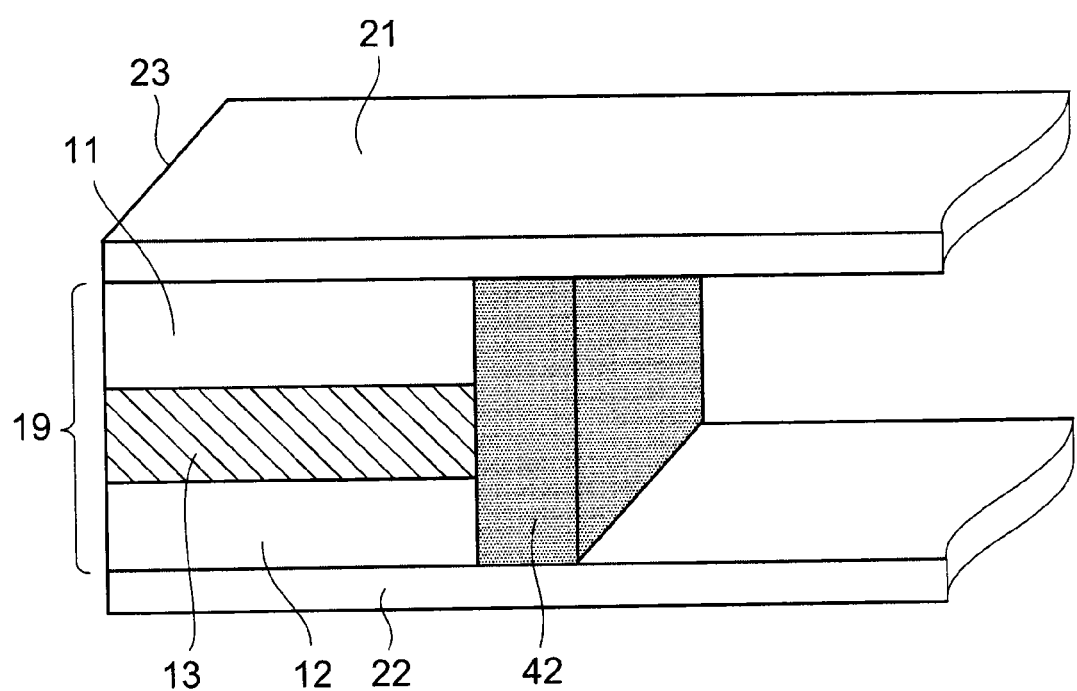
FIG. 6 is a perspective view illustrating a magnetic head according to a third embodiment.

FIG. 6 is a perspective view illustrating the magnetic head according to the third embodiment.

This embodiment is an example in which a strain introduction member 42 is connected to the device, in order to apply the strain introduced into the magneto-resistive effect device in a more controlled manner.

As illustrated in FIG. 6, in this embodiment, the strain introduction member 42 is provided adjacent to the magneto-resistive effect device 10, for example, on the surface of the stacked body 19 opposite the ABS surface 23. The strain introduction member 42 may be a part of an enclosure made from an insulating material used as a shield to electrically isolate or magnetically isolate the device. An internal stress is formed within the stacked body 19 by a mechanical property of the strain introduction member 42, for example, by thermal expansion of the strain introduction member 42. In this case, the strain is applied by using materials with different thermal expansion coefficients for the device part and the strain introduction member 42. Another example is to use a crystallographic mismatch between the stacked body 19 and the surrounding substance as the strain introduction member 42. Also, magnetostrictive expansion using a magnetic material having magnetostrictive properties can be used.

The strain introduced may be a compressive strain or a tensile strain.

Next, the effect of the magnetic head according to the third embodiment will be described.

In this embodiment, it is possible to apply strain to the device 10 in a controlled manner by introducing the strain introduction member 42 into the magneto-resistive effect device 10, so it is possible to control the bias of the magnetization directions of the two ferromagnetic layers with the spacer layer disposed therebetween.

In this way, it is possible to realize appropriate magnetization bias in the magneto-resistive effect device 10 with a thin film thickness suitable for narrow gaps. In other words, it is possible to realize a magnetic head suitable for high densification.

Fourth Embodiment

Next, a magnetic head according to a fourth embodiment will be described.

Figure 7A:
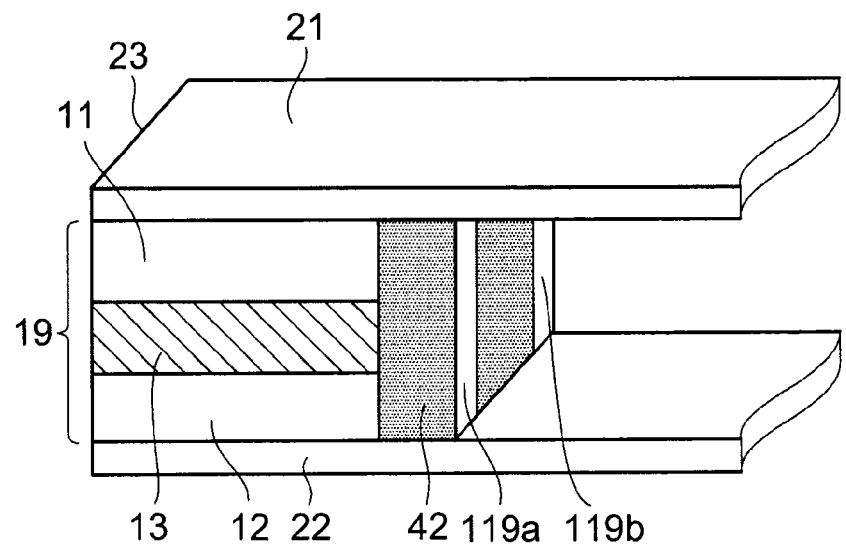
FIGS. 7A and 7B are perspective views illustrating a magnetic head according to a fourth embodiment.
Figure 7B:
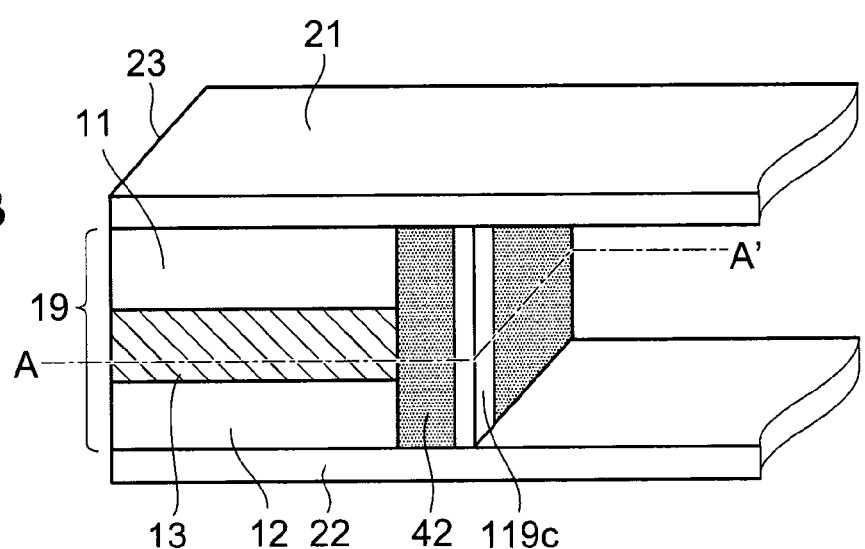
Figure 7C:
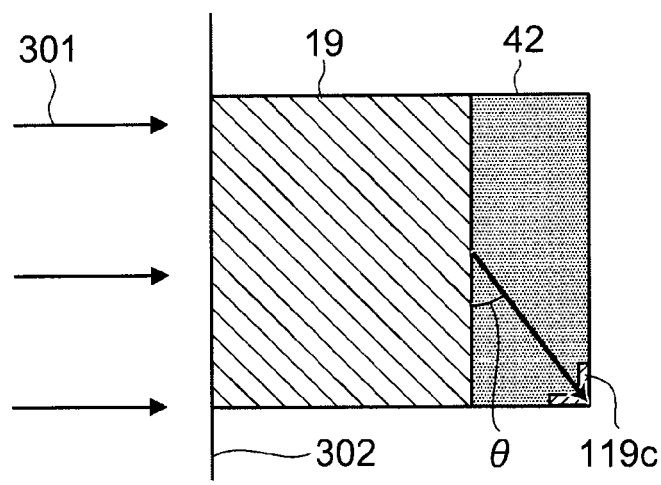
FIG. 7C is a cross-sectional view at the plane A-A' indicated on FIG. 7B.

FIGS. 7A and 7B are perspective views illustrating the magnetic head according to the fourth embodiment, and FIG. 7C is a cross-sectional view at the plane A-A' indicated on FIG. 7B.

As illustrated in FIG. 7A, in this embodiment, a piezoelectric material is used in the strain introduction member 42.

In order to apply a more actively controlled strain, rather than a passive strain application means such as the above thermal expansion, a piezoelectric material whose crystal deforms with the application of a voltage can be used as the strain introduction member 42.

The following materials are examples of specific materials having this type of voltage characteristic. Namely, silicon oxide ($SiO_2$), zinc oxide (ZnO), $KaC_4H_4O_6$, lead zirconate titanate (PZT: $Pb(Zr, Ti)O_3$), lithium niobate ($LiNbO_3$), lithium tantalate ($LiTaO_3$), lithium borate ($Li_2B_4O_7$), langasite ($La_3Ga_5SiO_{14}$), aluminum nitride (AlN), polyvinylidene difluoride (PVDF), gallium phosphate ($GaPO_4$), tourmaline, and so on. Also, additive elements or the like may be added to these piezoelectric materials as a base, to enhance their characteristics. In the case of these piezoelectric materials, the strain introduction member 42 includes electrodes 199a and 199b to apply a voltage to the strain introduction member 42, and by applying a voltage to them, it is possible to apply the strain.

For example, in the strain introduction member 42, the electrodes are provided on the surface on the opposite side of the surface in contact with the stacked body 19 of the device 10, and it is possible to apply the strain by applying a voltage.

These materials have insulating properties, so they can be brought into contact with the stacked body 19 of the device 10. By bringing the device and the strain introduction member directly into contact, it is possible to apply a greater strain.

In FIG. 7A, the electrodes 119a, 119b are disposed in locations on the strain introduction member 42 in order to apply the voltage, but the electrodes can be disposed in other locations. For example, as illustrated in FIG. 2C, if a straight line 302 normal to the direction of application of the external magnetic field 301 to the magneto-resistive effect device 10 is taken to be 0 degrees, when viewed from above the film face, when the angle θ between a tensile stress or a compressive stress and the straight line 302 is 45 degrees or 135 degrees, it is possible to realize an appropriate bias. Therefore, the electrodes for applying stress to the strain introduction member 42 are preferably provided at one end of the piezoelectric member, as illustrated in FIGS. 7B and 7C. In other words, when the straight line 302 normal to the direction of application of the external magnetic field 301 is taken to be 0 degrees, an electrode 119c is provided in a position at 45 degrees or 135 degrees when viewed from above the film face, a position that is capable of applying a stress to the magneto-resistive effect device 10 in a direction 45 degrees or 135 degrees when viewed from the ABS surface 23.

Next, the effect of the magnetic head according to the fourth embodiment will be described.

In this embodiment, a piezoelectric material is used as the strain introduction member 42, so it is possible to introduce an actively controlled strain, and it is possible to realize a magnetic head suitable for high density.

Fifth Embodiment

Next, a magnetic head according to a fifth embodiment will be described.

Figure 8:
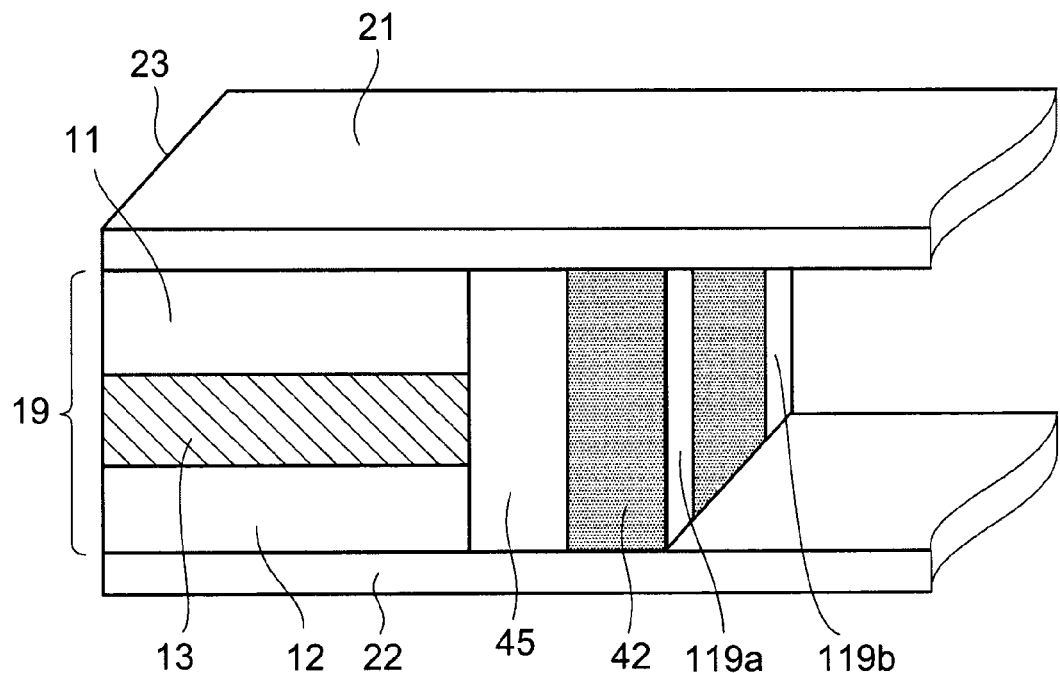
FIG. 8 is a perspective view illustrating a magnetic head according to a fifth embodiment.

FIG. 8 is a perspective view illustrating the magnetic head according to the fifth embodiment.

As illustrated in FIG. 8, in this embodiment, an insulating material 45 is provided between the strain introduction member 42 and the stacked body 19.

The piezoelectric material has inferior insulating properties compared with silicon oxide ($SiO_2$) with an amorphous structure, aluminum oxide ($Al_2O_3$) with an amorphous structure, and so on, that are normally used as the insulating material of the device 10, so after providing these common insulating materials around the device, the strain introduction member 42 is placed in contact with the outside thereof, with about 1 to 3 nm therebetween. Between the strain introduction member 42 and the stacked body 19, silicon oxide ($SiO_2$), aluminum oxide ($Al_2O_3$) is placed in contact. In each case, the strain introduction member 42 can be considered to be a bias application structure for controlling the magnetization directions of the two ferromagnetic layers 11 and 12 of the stacked body 19 of the device 10. In other words, in contrast to a conventional hard bias, in which the magnetization direction of the magnetic layer is controlled with a bias using a magnetic field, in this embodiment, a magnetic field is not used, but by using strain, which is a different physical quantity, it is possible to orient the magnetization of the two ferromagnetic layers 11 and 12 in different directions.

In this way, the bias to orient the magnetization directions of the two magnetic layers in different directions using a magnetic field was inevitably very difficult and complex, so realization was difficult. In contrast, in the method of this embodiment, by providing the top and bottom magnetic layers with opposite magnetostriction polarity, with the spacer layer disposed therebetween, and applying an external strain of single polarity, it is possible to bias the magnetization directions of the two ferromagnetic layers in different directions.

The effect of the magnetic head according to this embodiment is the same as described above, so the explanation is omitted.

Sixth Embodiment

Next, a magnetic head according to a sixth embodiment will be described.

Figure 9:
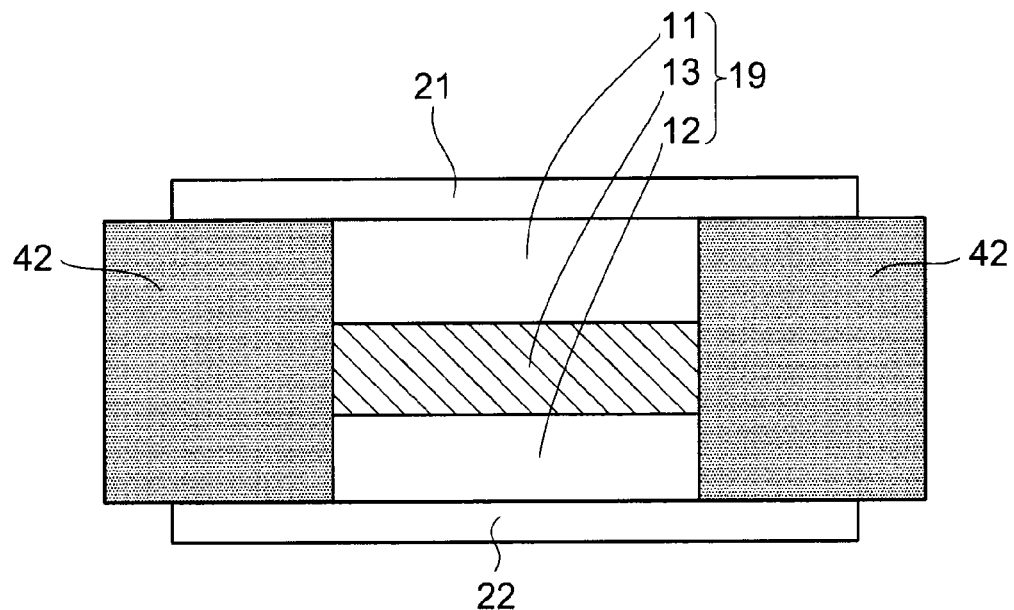
FIG. 9 is a perspective view illustrating a magnetic head according to a sixth embodiment.

FIG. 9 is a perspective view illustrating the magnetic head according to the sixth embodiment.

As illustrated in FIG. 9, in this embodiment, the strain introduction member 42 is located on the two side surfaces of the stacked body 19, apart from the ABS surface 23 and the surface opposite the ABS surface 23, with the stacking direction of the stacked body 19 taken to be vertical. Then, the stacked body 19 and the strain introduction members 42 are sandwiched between the top electrode 21 and the bottom electrode 22 in the vertical direction of the stacked body 19. In other words, the strain introduction members 42 are provided instead of a conventional hard bias film. A piezoelectric material can be used. Specific examples of the piezoelectric material in this case are the same as those materials previously described.

If necessary, in addition to the method of biasing by applying strain according to this embodiment, it is possible to provide a hard bias film using a magnetic field to bias the magnetization of the ferromagnetic layers 11 and 12 in accordance with the circumstances. In this case, a hybrid bias structure can be considered, in which a hard bias layer is disposed in the same location as when using a magnetic field, and the strain introduction members 42 are provided to the left and right separated from the hard bias film, when viewed from the ABS surface 23.

The effect of the magnetic head according to this embodiment is the same as described above, so the explanation is omitted.

Seventh Embodiment

Next, a magnetic head according to a seventh embodiment will be described.

Figure 10:
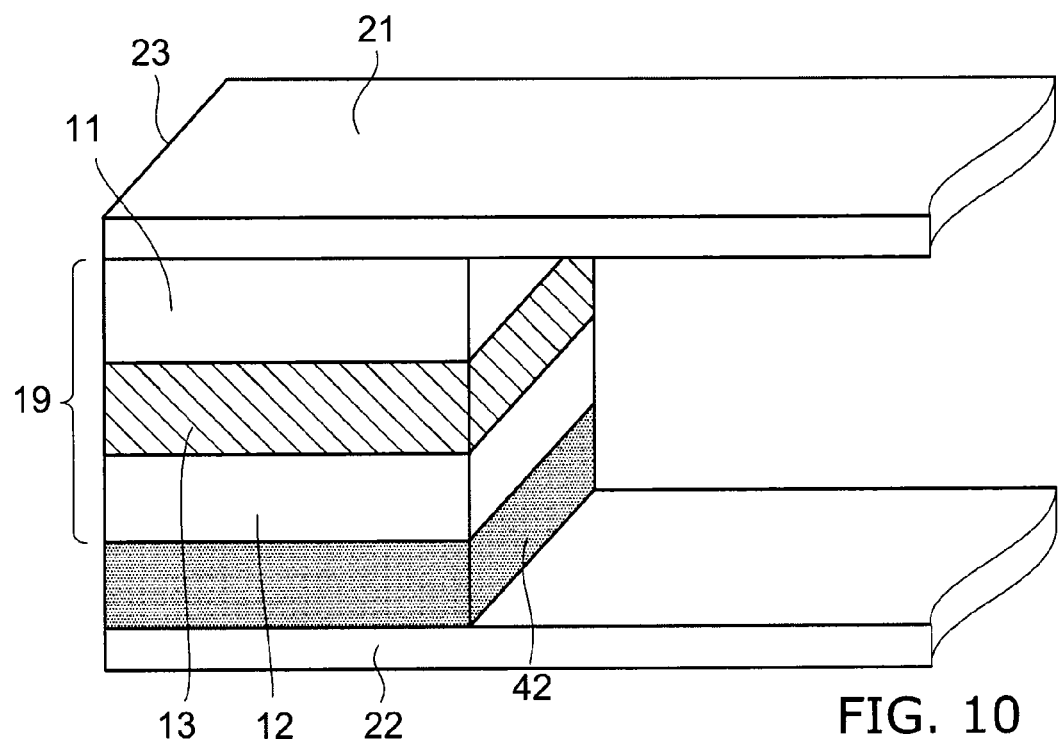
FIG. 10 is a perspective view illustrating a magnetic head according to a seventh embodiment.

FIG. 10 is a perspective view illustrating the magnetic head according to the seventh embodiment.

As illustrated in FIG. 10, in this embodiment, the strain introduction member 42 is inserted between the stacked body 19 and the bottom electrode 22. The strain introduction member 42 may also be inserted between the stacked body 19 and the top electrode 21.

In the case of FIG. 10, the strain introduction member 42 is used in combination with the electrode to pass current through the stacked body 19 of the device 10. Therefore a piezoelectric material is not suitable as the strain introduction member 42.

Next, operation of the magnetic head according to the seventh embodiment will be described.

In this embodiment, the strain introduction member 42 is inserted between the stacked body 19 and the electrode in order to further increase the strain introduced into the magneto-resistive effect device 10. A characteristic strain is generated in the device by the strain introduction member 42. Also, the strain introduction member 42 causes a strain in the device as an external factor. The strain introduction member 42 is stacked on the stacked body 19, so it is possible to introduce more strain in the in-plane direction.

The device characteristic strain and the strain due to external factor are the same as described for the third embodiment, so the explanation is omitted here.

Eighth Embodiment

Next, a magnetic head according to an eighth embodiment will be described.

Figure 11:
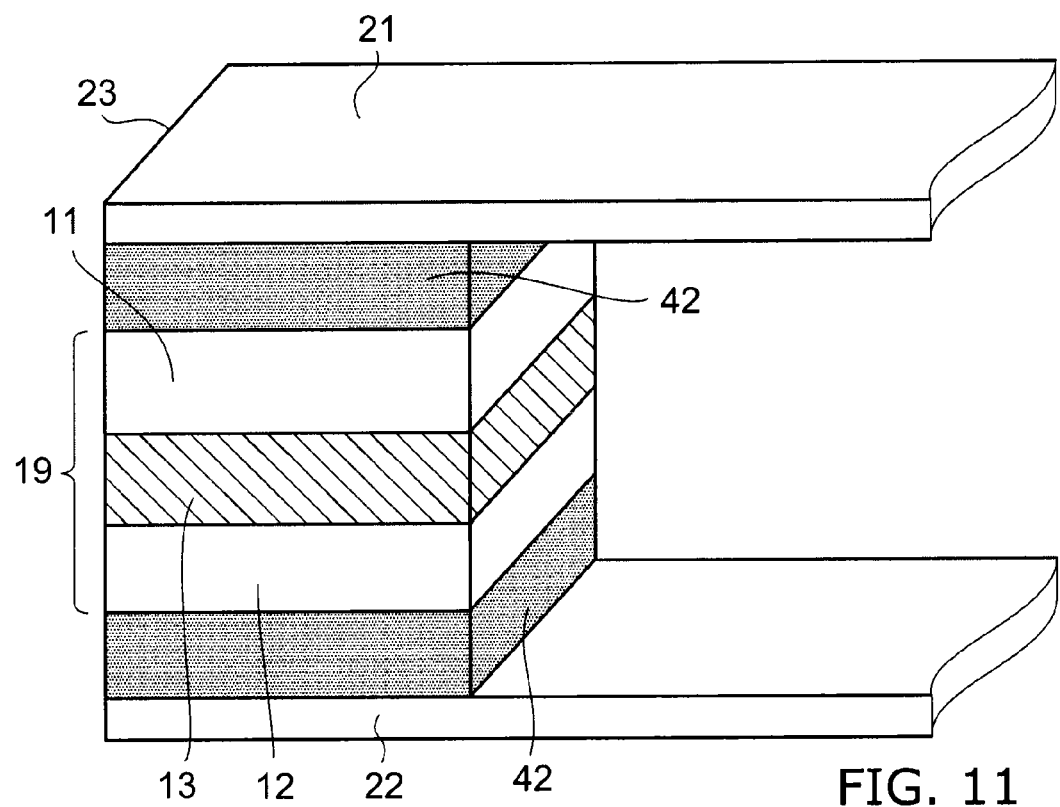
FIG. 11 is a perspective view illustrating a magnetic head according to an eighth embodiment.

FIG. 11 is a perspective view illustrating the magnetic head according to the eighth embodiment. The difference between the seventh embodiment and the eighth embodiment is that, in the seventh embodiment, the strain introduction member 42 is a single layer, and in contrast in the eighth embodiment there are two layers, disposed between the stacked body 19 and each of the pair of electrodes.

As illustrated in FIG. 11, in the eighth embodiment, the strain introduction member 42 is inserted between the stacked body 19 and the top electrode 21, and between the stacked body 19 and the bottom electrode 22.

In the case of FIG. 11, the strain introduction members 42 are used in combination with the electrodes to pass current through the stacked body 19, so an insulating material cannot be used. Therefore a piezoelectric material is not suitable as the strain introduction member 42.

Next, operation of the magnetic head according to the eighth embodiment will be described.

In the eighth embodiment also, a strain introduction member 42 is inserted between the stacked body 19 and each of the pair of electrodes in order to further increase the strain introduced into the magneto-resistive effect device. A characteristic strain is generated in the device by the strain introduction members 42. Unlike the seventh embodiment, both the first and second magnetic layers are in contact with the strain introduction members 42.

The device characteristic strain and the strain due to external factor are the same as described above.

Ninth Embodiment

Next, a magnetic head according to a ninth embodiment will be described.

Figure 12:
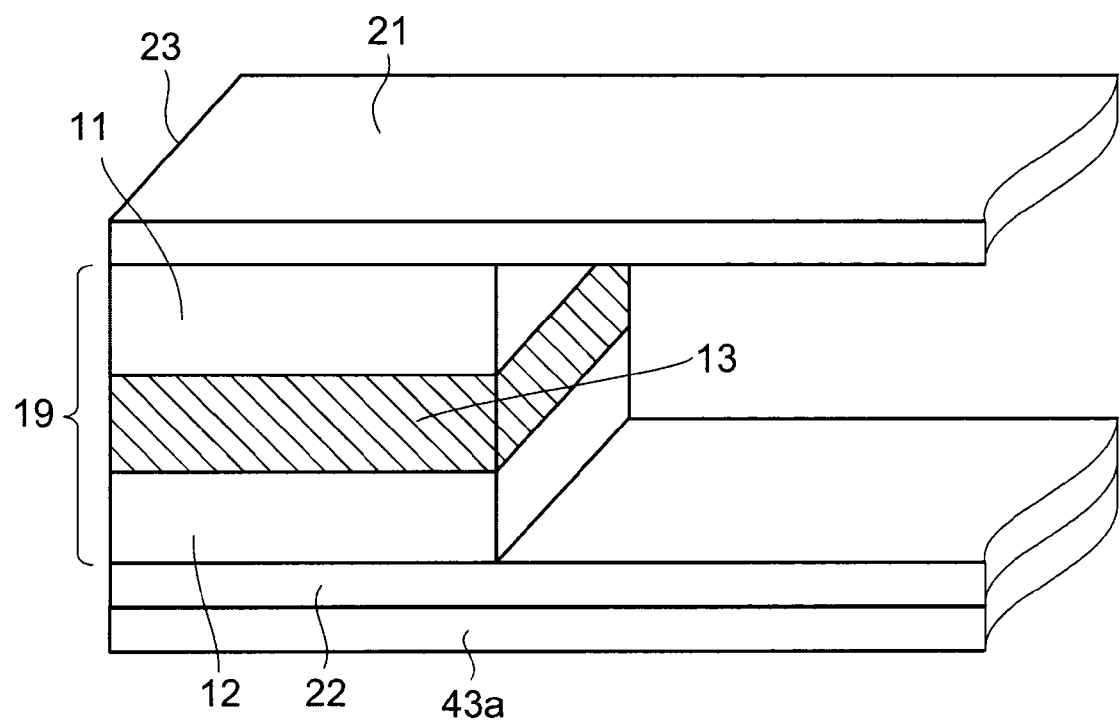
FIG. 12 is a perspective view illustrating a magnetic head according to a ninth embodiment.

FIG. 12 is a perspective view illustrating the magnetic head according to the ninth embodiment.

As illustrated in FIG. 12, in this embodiment, the magneto-resistive effect device 10 is provided on a substrate 43a. In other words, the bottom electrode 22 is provided on the substrate 43a, and the stacked body 19 is provided on the bottom electrode 22. The top electrode 21 is provided on the stacked body 19.

Next, operation of the magnetic head according to the ninth embodiment will be described.

In this embodiment, the magneto-resistive effect device 10 is provided on the substrate 43a. The substrate 43a may be the strain introduction member 42. For example, if the magneto-resistive effect device 10 is formed on the substrate 43a after introducing a strain into the substrate 43a, strain is introduced into the stacked body 19.

Next, the effect of the magnetic head according to the ninth embodiment will be described.

In the ninth embodiment, the substrate 43a can be the strain introduction member 42, so there is no necessity to provide a dedicated strain introduction member 42 as in the first through third variations, so the magnetic head can be miniaturized.

Tenth Embodiment

Next, a tenth embodiment will be described. This embodiment relates to a magnetic head gimbal assembly.

Figure 13A:
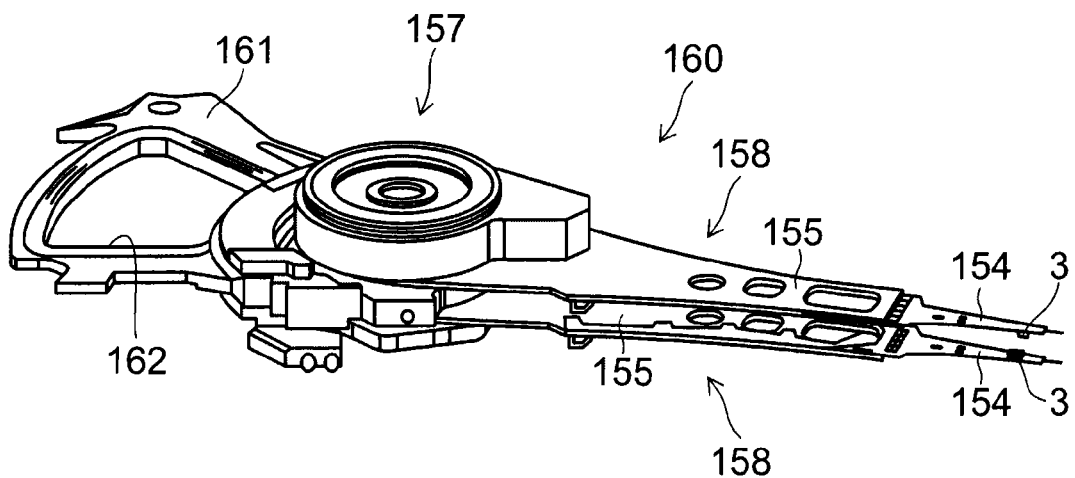
FIGS. 13A and 13B are perspective views illustrating a magnetic head gimbal assembly according to a tenth embodiment.
Figure 13B:
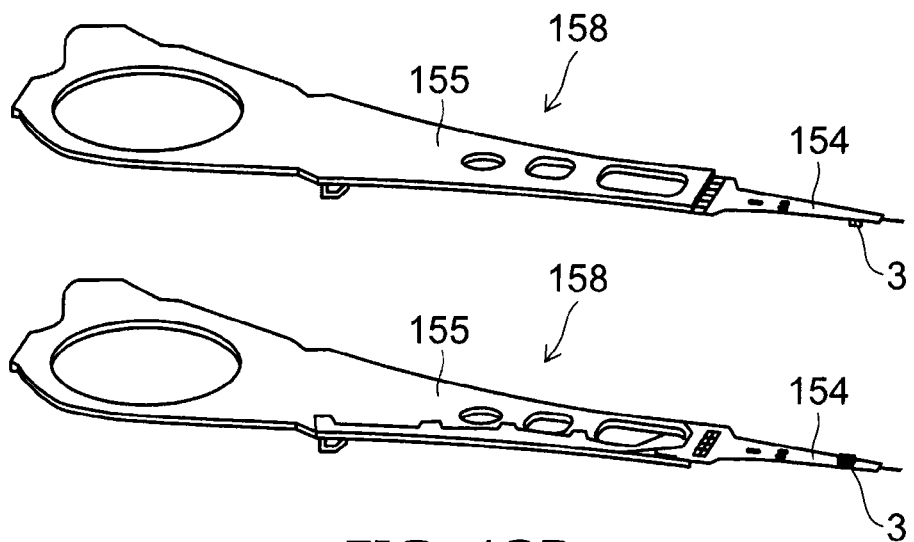

FIGS. 13A and 13B are perspective views illustrating the magnetic head gimbal assembly according to the tenth embodiment.

As illustrated in FIG. 13A, a head stack assembly 160 includes a bearing part 157, a magnetic head gimbal assembly 158 extending from the bearing part 157, and a support frame 161 extending from the bearing part 157 in a direction opposite that of the magnetic head gimbal assembly 158 and that supports a coil 162 of a voice coil motor.

Also, as illustrated in FIG. 13B, the magnetic head gimbal assembly 158 includes an actuator arm 155 extending from the bearing part 157, and a suspension 154 extending from the actuator arm 155. A head slider 3 is mounted on a tip of the suspension 154. Then the magnetic head according to the embodiment is mounted on the head slider 3. In other words, the magnetic head gimbal assembly 158 according to this embodiment includes the magnetic head according to the embodiment, the head slider 3 into which the magnetic head is mounted, the suspension 154 mounted at one end of the head slider 3, and the actuator arm 155 connected to the other end of the suspension 154. The suspension 154 includes leads (not illustrated on the drawings) for writing and reading signals, for a heater for adjusting the floating height, and for a spin torque oscillator, for example, and so on. These leads are electrically connected to the electrodes of the magnetic head incorporated into the head slider 3.

Eleventh Embodiment

Figure 14:
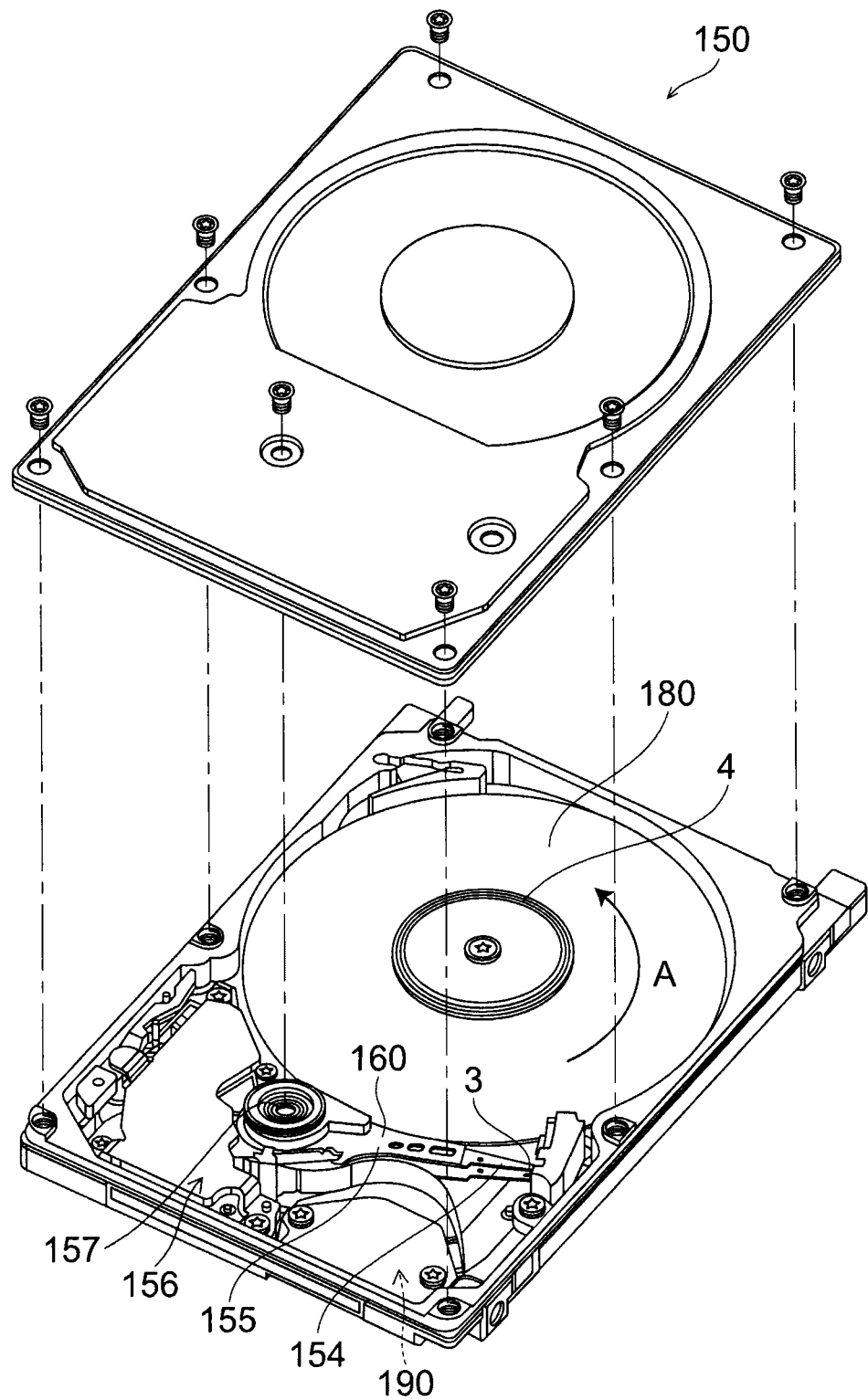
FIG. 14 is a perspective view illustrating a magnetic recording/reproduction device according to an eleventh embodiment.

FIG. 14 is a perspective view illustrating the magnetic recording/reproduction device according to an eleventh embodiment.

As illustrated in FIG. 14, a magnetic recording/reproduction device 150 according to the eleventh embodiment is a rotary actuator-type device. In this drawing, a recording medium disk 180 is mounted on a spindle motor 4, and is rotated in the direction of the arrow symbol A by a motor, which is not illustrated on the drawings, in response to a control signal from a drive device control unit, which is not illustrated on the drawings. The magnetic recording/reproduction device 150 according to this embodiment may include a plurality of recording medium disks 180. The head slider 3 that records and reproduces information stored on the recording medium disk 180 is mounted on the tip of the suspension 154 in thin film form. Here, a magnetic head according to any of the embodiments that have been already explained, for example, is mounted near the tip of the head slider 3.

When the recording medium disk 180 rotates, the pressing pressure from the suspension 154 and the pressure generated by the media opposing face (ABS) of the head slider 3 balance, and the media opposing face of the head slider 3 is maintained at a predetermined floating height from the surface of the recording medium disk 180. The contact between the head slider 3 and the recording medium disk 180 may be "moving contact type".

The suspension 154 is connected to a first end of the actuator arm 155 which has a bobbin portion or the like for supporting a drive coil (not illustrated). A voice coil motor 156, which is a type of linear motor, is provided on a second end of the actuator arm 155. The voice coil motor 156 can include a drive coil (not illustrated) that is wound around the bobbin portion of the actuator arm 155, and a magnetic circuit with a permanent magnet and a counter yoke which are disposed opposite to one another so as to sandwich the drive coil.

The actuator arm 155 is supported by ball bearings (not illustrated) provided at two locations, at the top and bottom of the bearing part 157, and thereby the actuator arm 155 can be rotated and slid freely by the voice coil motor 156. As a result, it is possible to move the magnetic head to any position on the recording medium disk 180.

Also, a signal processing unit 190 that writes and reads signals to and from the magnetic recording media using the magnetic head is provided. The signal processing unit 190 is provided on the reverse side (of the drawing) of the magnetic recording/reproduction device 150. Input and output wires of the signal processing unit 190 are connected to an electrode pad of a magnetic head gimbal assembly that constitutes a part of the head stack assembly 160, and is thereby electrically connected to the magnetic head.

The magnetic recording/reproduction device 150 according to this embodiment uses the head gimbal assembly 158 that includes a magnetic head that includes the magneto-resistive effect device as described above, manufactured in accordance with at least any of the first through third embodiments of the invention, so it can reliably read information recorded magnetically on a magnetic disk 200 at high memory density, using the MR rate of change.

Twelfth Embodiment

Figure 15:
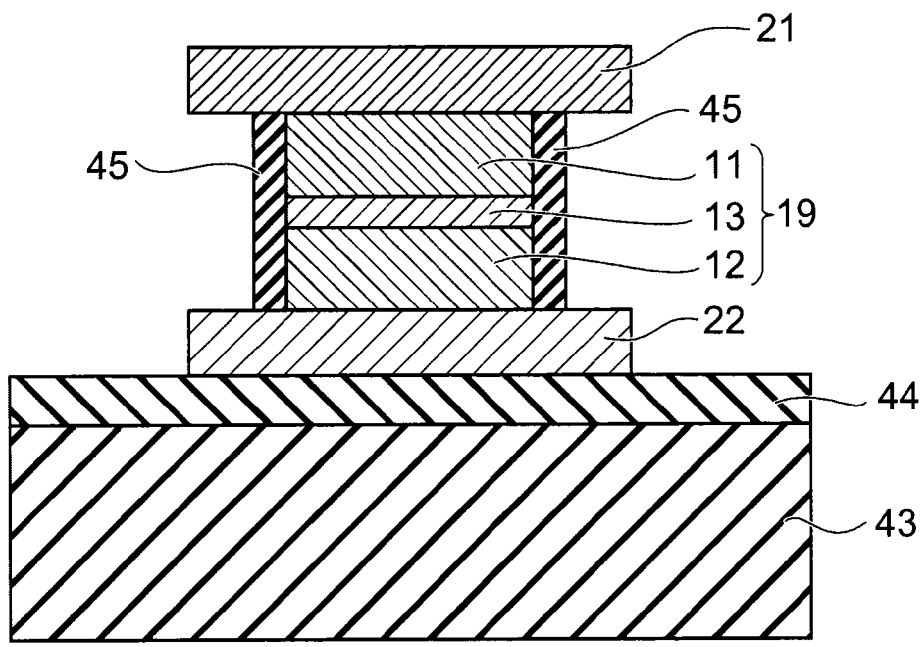
FIG. 15 is a cross-sectional view illustrating a strain sensor according to a twelfth embodiment.

Next, a twelfth embodiment will be described.
This embodiment relates to a strain sensor.
FIG. 15 is a cross-sectional view illustrating the strain sensor according to the twelfth embodiment.

As illustrated in FIG. 15, in the strain sensor according to this embodiment, a flexible substrate 43 is provided. A priming layer 44 is provided on the flexible substrate 43. The priming layer 44 may be configured from a plurality of layers such as seed layers (not illustrated) or pinning layers (not illustrated). These several layers can be omitted by using a special thin film structure. By providing the priming layer 44, it is possible to suppress defects that are not necessary for the flexible substrate 43, for example, surface roughness. Also, by providing the seed layers, it is possible to control the important crystal direction for forming the magnetic layer/spacer layer/magnetic layer. In addition, by providing the pinning layers, it is possible to fix the magnetization direction of a pinned layer. The priming layer 44 may be a conductive material.

The bottom electrode 22 is provided on the priming layer 44, and the magneto-resistive effect device 10 with the stacked body 19 structure is provided thereupon. The magneto-resistive effect device 10 is the same as the magneto-resistive effect device according to the first embodiment, so it is configured from the ferromagnetic layer 11, the ferromagnetic layer 12, and the spacer layer 13 disposed between the ferromagnetic layer 11 and the ferromagnetic layer 12. The polarities of the magnetostriction of the ferromagnetic layer 11 and the ferromagnetic layer 12 are positive and negative, constituted from materials with different polarity magnetostriction coefficient. However, the ferromagnetic layer 11 and the ferromagnetic layer 12 have opposite magnetostrictive effects. In other words, one of the ferromagnetic layer 11 and the ferromagnetic layer 12 is a ferromagnetic layer with a positive magnetostriction coefficient, and the other is a ferromagnetic layer with a negative magnetostriction coefficient.

The top electrode 21 is provided on the stacked body 19, forming a CPP structure in which current flows in the stacking direction of the stacked body. In other words, the sense current flows vertically through the stacked body.

In other to protect the magneto-resistive effect device 10, and in order to electrically isolate the magneto-resistive effect device 10 from other members, the periphery of the magneto-resistive effect device 10 is covered with an insulating material 45.

The following are specific examples of materials with different magnetostriction polarity of the ferromagnetic layer 11 and the ferromagnetic layer 12 of the magneto-resistive effect device 10.

Normally, the magnetostriction of a magnetic layer is determined by the composition of the magnetic layer. The general trends of these have been investigated in many publications. However, the actual magnetostriction is greatly affected by the materials adjacent to the magnetic layer.

If an oxide material is used as the spacer layer (a tunnel barrier layer such as magnesium oxide (MgO) or a CCP layer), when a magnetic layer that includes cobalt iron (CoFe) or the like is used at the interface with the spacer layer, the top and bottom magnetic layers normally have positive magnetostriction within 1 to 2 nm of the interface. This is because magnetic oxide layers such as $CoFeBO_x$, $CoO_x$, $NiO_x$ and $FeO_x$, and so on are materials that have positive magnetostriction. Next, the ferromagnetic layers 11 and 12 are given different positive and negative magnetostriction. It is comparatively easy to form a ferromagnetic layer with positive magnetostriction. Therefore, in order to form negative magnetostriction, by stacking a magnetic layer with large negative magnetostriction onto the oxide interfacial layer of the oxide layer that has positive magnetostriction, the magnetic layer with negative magnetostriction can be formed as the total magnetic layer. Large negative magnetostriction can be achieved using a nickel (Ni) rich alloy. Examples include Ni, NiFe alloy (including not less than 85 atomic percent Ni), SmFe, and so on. When the magnetic material is formed from a plurality of layers so that they act as a magnetically integral magnetic layer, the magnetostriction of the magnetic layer is determined by the total stacked film constitution of the magnetic layers (on the other hand, the other magnetic layer with the nonmagnetic layer disposed therebetween functions as a separate magnetic layer, so the magnetostriction is defined as a separate value).

A specific example of the stacked film constitution of the ferromagnetic layer 11/spacer layer 13/ferromagnetic layer 12 is a stacked film of $Co_{90}Fe_{10}$/CoFeB/MgO/CoFeB/$Ni_{95}Fe_5$, with film thicknesses of 2 nm/1 nm/1.5 nm/1 nm/2 nm respectively. Here, the $Co_{90}Fe_{10}$/CoFeB layers function as a single ferromagnetic layer that exhibits positive magnetostriction, and the CoFeB/$Ni_{95}Fe_5$ layers function as a single ferromagnetic layer that exhibits negative magnetostriction. The MgO layer is the spacer layer.

Next, operation of the strain sensor according to the twelfth embodiment will be described.

Figure 16:
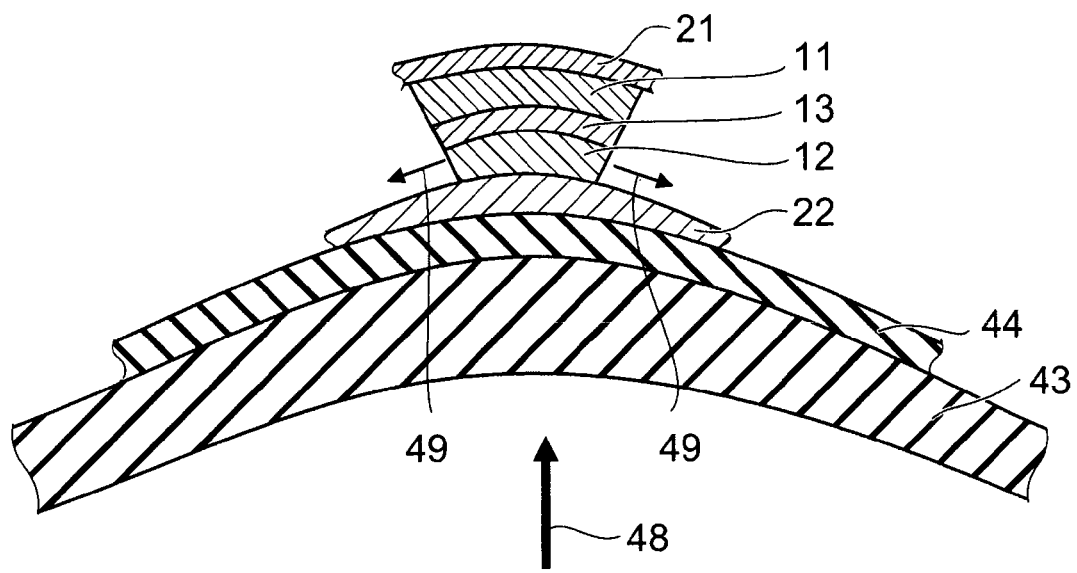
FIG. 16 is a cross-sectional view illustrating the operation of the strain sensor according to the twelfth embodiment.
Figure 17:
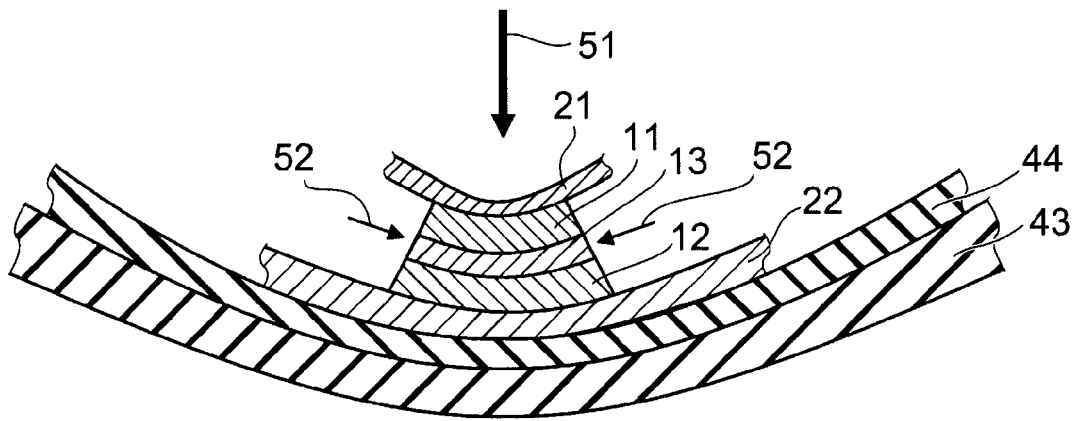
FIG. 17 is a cross-sectional view illustrating the operation of the strain sensor according to the twelfth embodiment.

FIGS. 16 and 17 are cross-sectional views illustrating the operation of the strain sensor according to the twelfth embodiment.

As illustrated in FIG. 16, when an upward acting stress 48 is applied to the flexible substrate 43, the outside of the flexible substrate 43 is stretched and rounded, and as a result a tensile strain 49 is applied to the magneto-resistive effect device 10 fixed to the flexible substrate 43.

On the other hand, as illustrated in FIG. 17, when a downward acting stress 51 is applied to the flexible substrate 43, the flexible substrate 43 is bent to the inside, and as a result a compressive strain 52 is applied to the device 10.

Figure 18A:
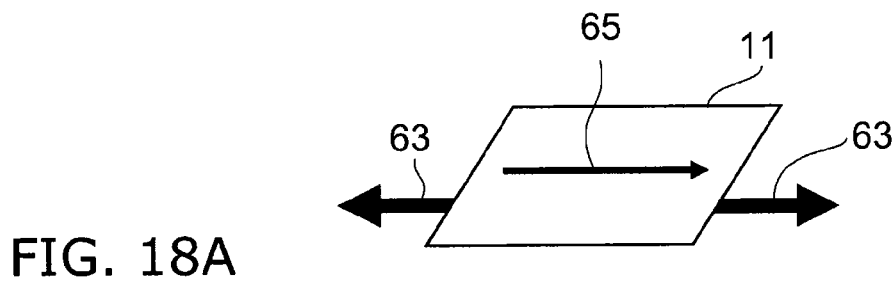
FIGS. 18A and 18B illustrate the operation of the strain sensor according to the twelfth embodiment.
Figure 18B:
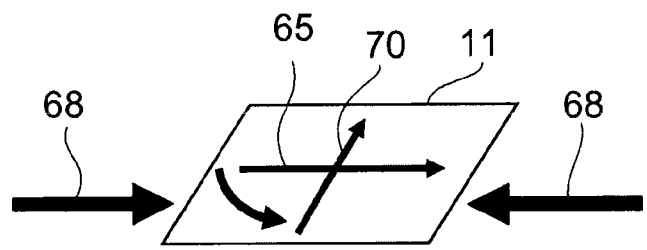

FIGS. 18A and 18B illustrate the operation of the strain sensor according to the twelfth embodiment, FIG. 18A illustrates a case in which a tensile strain is applied, and FIG. 18B illustrates a case in which a compressive strain is applied.

FIGS. 18A and 18B illustrate only the two ferromagnetic layers of the magneto-resistive effect device 10.

As stated above, the stacked body 19 is disposed in the strain sensor according to the twelfth embodiment, and the stacked body 19 includes the ferromagnetic layer 11 and the ferromagnetic layer 12.

As illustrated in FIGS. 18A and 18B, in the magneto-resistive effect device 10, of the two ferromagnetic layers, the top layer is the ferromagnetic layer 11 with a positive magnetostriction coefficient, and the bottom layer is the ferromagnetic layer 12 with a negative magnetostriction coefficient. Also, prior to application of the strain, the magnetization directions 65 and 66 of the ferromagnetic layers 11 and 12 are parallel. In other words, the resistance state of the device 10 is the low resistance state. Then, as illustrated in FIG. 18A, when a tensile strain 63 is applied to the device in the same direction as the magnetization directions 65 and 66, the magnetization direction 65 of the ferromagnetic layer 11 does not change, but the magnetization direction 66 of the ferromagnetic layer 12 changes to a magnetization direction 67 normal to the tensile strain. As a result, the magnetization directions of the two ferromagnetic layers become orthogonal to each other. Then the resistance state of the device 10 changes to the intermediate resistance state.

Also, as illustrated in FIG. 18B, when a compressive strain 68 is applied to the device 10 in the same direction as the magnetization directions 65 and 66, the magnetization direction 65 of the ferromagnetic layer 11 changes to a magnetization direction 70 normal to the compressive strain, but the magnetization direction 66 of the ferromagnetic layer 12 does not change. As a result, the magnetization directions of the two ferromagnetic layers become orthogonal to each other. Then the resistance state of the device 10 changes to the intermediate resistance state.

Next, the method of measuring the magnitude of the strain using the strain sensor is explained.

First, the strain sensor is placed on the location where the strain is to be measured. Prior to application of the strain to the strain sensor, the magnetization directions of the ferromagnetic layers 11 and 12 are parallel. Then, the sense current is passed between the electrodes 21 and 22, to determine the resistance state of the stacked body 19. As stated previously, as long as there is no strain applied to the strain sensor, the resistance state of the stacked body 19 will be the low resistance state.

Next, it is assumed that the resistance state becomes the intermediate resistance state. In this case, it can be determined that the magnetization direction of the ferromagnetic layer 11 and the magnetization direction of the ferromagnetic layer 12 of the stacked body 19 have changed to become orthogonal. In other words, it can be determined that a strain has been applied to the substrate 43 sufficient to make the magnetization direction of the ferromagnetic layer 11 and the magnetization direction of the ferromagnetic layer 12 orthogonal. The resistance state changes in accordance with the angle between the magnetization direction of the ferromagnetic layer 11 and the magnetization direction of the ferromagnetic layer 12. Therefore, if the relationship between the resistance state and the amount of strain applied to the substrate 43 is determined in advance by another method, it is possible to measure the amount of strain applied to the substrate 43 by measuring the magnitude of the sense current.

In FIGS. 18A and 18B, the directions of application of the tensile strain and the compressive strain are the same as the magnetization directions of the ferromagnetic layers, but are not limited thereto.

The direction of the strain is not important for exhibiting the function of the magneto-resistive effect device 10. This is because the resistance state changes for any strain direction.

Figure 19A:
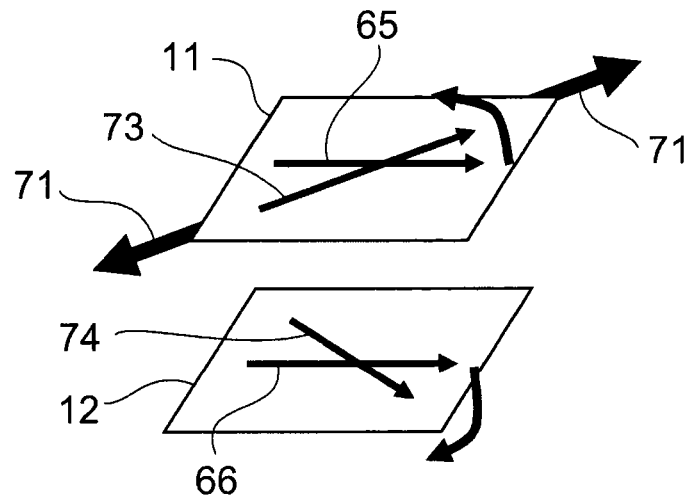
FIGS. 19A, 19B, and 19C illustrate the operation of the strain sensor according to the twelfth embodiment.
Figure 19B:
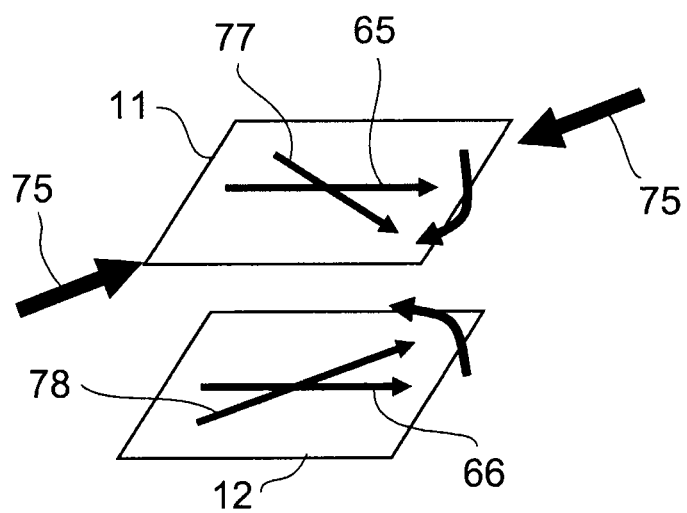
Figure 19C:
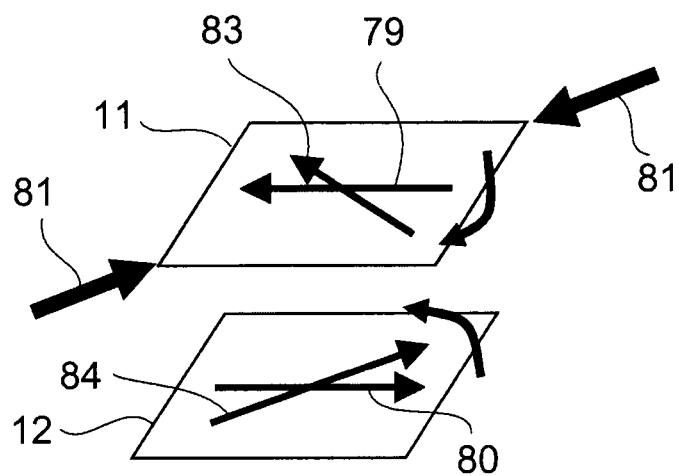

FIGS. 19A, 19B, and 19C illustrate the operation of the strain sensor according to the twelfth embodiment, FIG. 19A illustrates a case in which a tensile strain is applied in an arbitrary direction, FIG. 19B illustrates a case in which a compressive strain is applied in an arbitrary direction, and FIG. 19C illustrates a case in which a compressive strain is applied and prior to application of the strain the magnetization directions of the two ferromagnetic layers are anti-parallel.

As illustrated in FIG. 19A, when a tensile strain 71 is applied to the device 10 at an arbitrary angle to the magnetization directions of the ferromagnetic layer 11 and the ferromagnetic layer 12, the magnetization direction 65 of the ferromagnetic layer 11 rotates towards the direction of the tensile strain and changes to the magnetization direction 73, and the magnetization direction 66 of the ferromagnetic layer 12 rotates orthogonal to the direction of the tensile strain and changes to the magnetization direction 74. As a result, the magnetization directions of the two ferromagnetic layers become orthogonal to each other. Then the resistance state of the device 10 changes to the intermediate resistance state.

Also, as illustrated in FIG. 19B, when a compressive strain 75 is applied to the device 10 at an arbitrary angle to the magnetization directions of the ferromagnetic layer 11 and the ferromagnetic layer 12, the magnetization direction 65 of the ferromagnetic layer 11 rotates orthogonal to the direction of the compressive strain and changes to the magnetization direction 77, and the magnetization direction 66 of the ferromagnetic layer 12 rotates towards the direction of the compressive strain and changes to the magnetization direction 78. As a result, the magnetization directions of the two ferromagnetic layers become orthogonal to each other. Then the resistance state of the device 10 changes to the intermediate resistance state.

In this way, the resistance state of the device 10 changes with a strain in an arbitrary direction, so it is possible to detect the magnitude of the strain.

Also, even when the initial state of the magnetization directions of the two ferromagnetic layers prior to application of the strain is antiparallel, it is possible to detect the strain of the substrate 43.

As illustrated in FIG. 19C, the initial magnetization directions 79 and 80 of the ferromagnetic layer 11 and the ferromagnetic layer 12 are antiparallel. In other words, the resistance state of the device 10 is the high resistance state. Then, for a compressive strain 81 at an arbitrary angle, the magnetization directions 79 and 80 rotate to the direction orthogonal to and the direction towards the compressive strain respectively, and change to the magnetization directions 83 and 84. As a result, the magnetization directions of the two ferromagnetic layers become orthogonal to each other. Then the resistance state of the device 10 changes to the intermediate resistance state. Hence, the initial magnetization directions of the ferromagnetic layers are not important for exhibiting the function of the magneto-resistive effect device 10.

Next, the effect of the strain sensor according to the twelfth embodiment will be described.

The strain sensor according to this embodiment can detect either a tensile strain or a compression strain. Also, it is possible to detect strain at an arbitrary angle to the magnetization direction of the magneto-resistive effect device 10 of the strain sensor. Also, it is possible to detect strain regardless of the initial magnetization direction of the magneto-resistive effect device, so it is possible to broaden the options for material of the ferromagnetic layers. Therefore, a single strain sensor according to this embodiment can detect strain as described above, so miniaturization is possible.

Variation of the Twelfth Embodiment

Next, a variation of the strain sensor according to a twelfth embodiment will be described.

Figure 20:
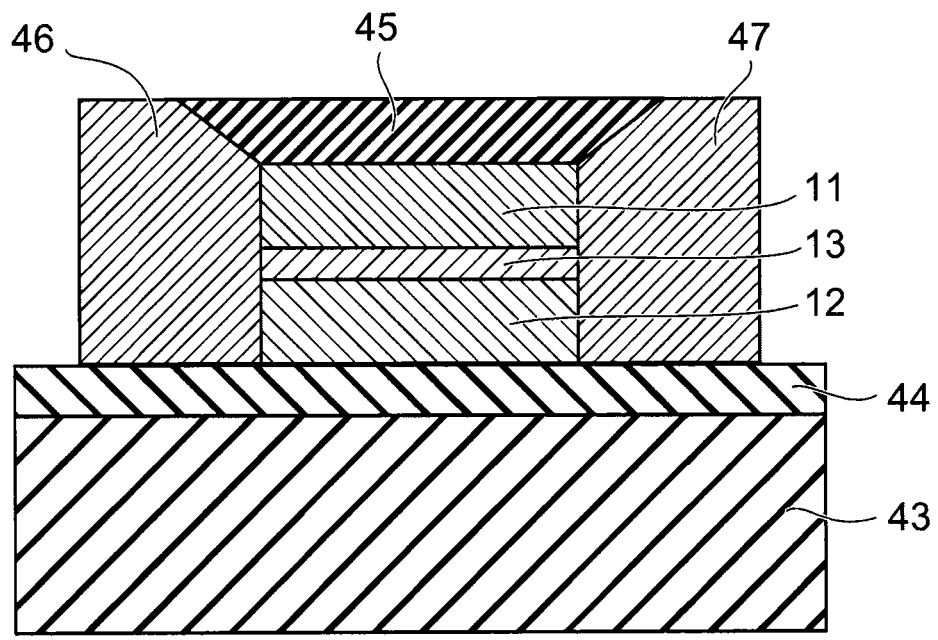
FIG. 20 is a cross-sectional view illustrating a variation of the strain sensor according to the twelfth embodiment.

FIG. 20 is a cross-sectional view illustrating the variation of the strain sensor according to the twelfth embodiment.

As illustrated in FIG. 20, in this variation, electrodes 46, 47 are provided on two sides sandwiching the stacked body 19.

Therefore, the sense current flows in the in-plane direction of the stacked body. In this embodiment, the device is covered with insulating material from above. The configuration, operation and effect of this embodiment other than that described above is the same as the third embodiment as described previously.

Thirteenth Embodiment

Next, a strain sensor according to a thirteenth embodiment will be described.

Figure 21:
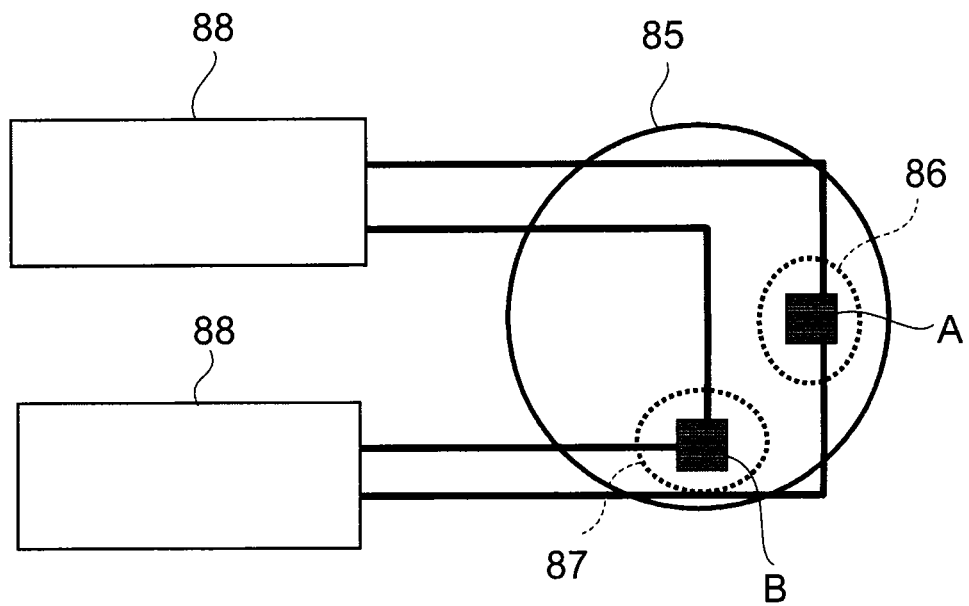
FIG. 21 is a cross-sectional view illustrating a strain sensor according to a thirteenth embodiment.

FIG. 21 is a cross-sectional view illustrating the strain sensor according to the thirteenth embodiment.

As illustrated in FIG. 21, the strain sensor according to this embodiment includes at least two magneto-resistive effect devices A, B. The two devices A, B are formed at two locations on a circular shaped membrane 85. The locations are such that the distances from the center of the circular shape to the two fixing locations are equal, and the angle between the directions from the center of the circular shape towards the two fixing locations is 90°. In other words, as illustrated in FIG. 21, one device A is provided at a location 86 at 3 o'clock on a clock viewed from above the circular shaped membrane 85, and the other device B is provided at a location 87 at 6 o'clock.

In this embodiment, the material of the substrate 43 is, for example, a thinly etched silicon that can easily bend. The substrate 43 has flexibility, and includes the membrane 85 to which the stacked body 19 is fixed and a supporting part that supports the membrane 85. However, provided it is possible to provide both the flexible membrane 85 and the supporting part, a flexible substrate other than silicon as described later can be used. Such a material can include ABS resin, cycloolefin-based resin, ethylene-propylene-based rubber, polyamide, polyamide-imide resin, polybenzimidazole, polybutylene terephthalate, polycarbonate, polyethene, PEEK, polyetherimide, polyethylene imine, polyethylene naphthalate, polyester, polysulfone, polyethylene terephthalate, phenol formaldehyde resin, polyimide, polymethyl methacrylate, polymethylpentene, polyoxymethylene, polypropylene, m-phenyl ether, poly(para-phenylene sulfide), para-aramid, polystyrene, polysulfone, polyvinyl chloride, polytetrafluoroethylene, perfluoroalkoxy, FEP, ETFE, polyethylene chloro trifluoro ethylene, polyvinylidene difluoride, melamine-formaldehyde, liquid crystal polymer, urea-formaldehyde, and so on.

Controllers 88 are provided around the membrane 85, and the controllers 88 are electrically connected to the devices A, B. The resistance states of the devices A, B are measured by the controllers 88.

Next, operation of the strain sensor according to the thirteenth embodiment will be described.

Figure 22A:
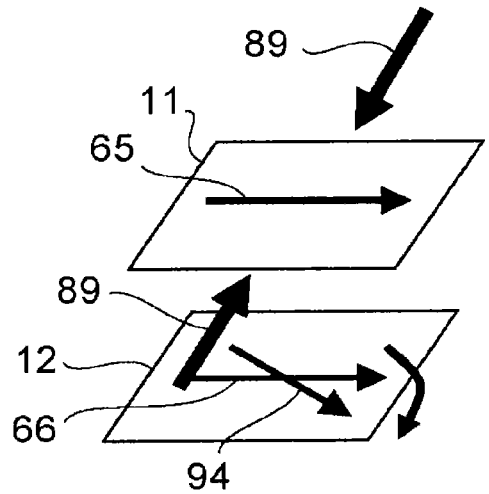
FIGS. 22A through 22D illustrate the operation of the strain sensor in accordance with the thirteenth embodiment.
Figure 22B:
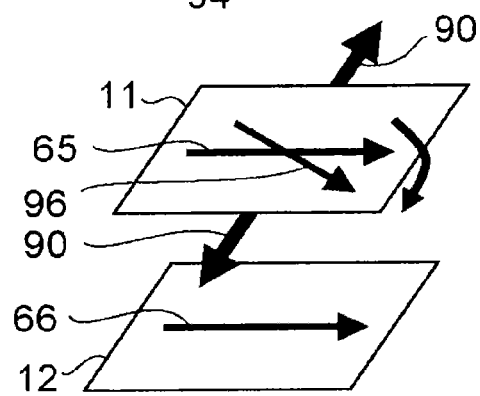
Figure 22C:
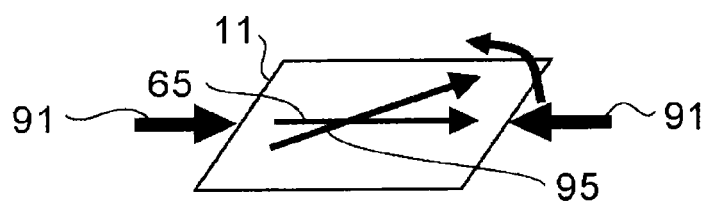
Figure 22D:
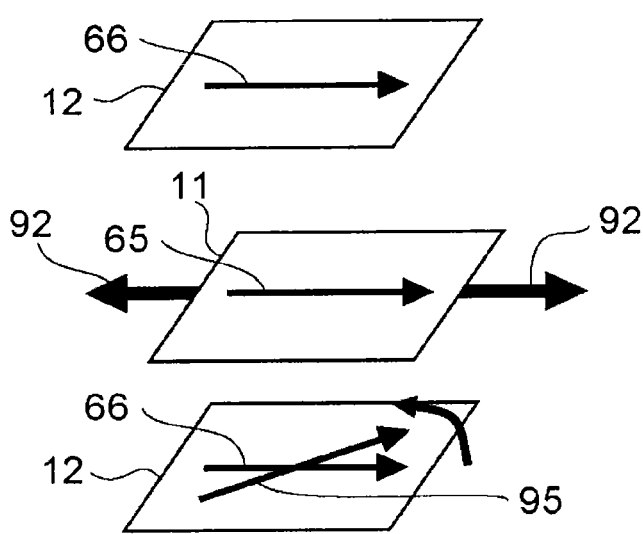

FIGS. 22A through 22D illustrate the operation of the strain sensor in accordance with the thirteenth embodiment, FIG. 22A illustrates a case where a compressive strain is applied to the device A, FIG. 22B illustrates a case where a tensile strain is applied to the device A, FIG. 22C illustrates a case where a compressive strain is applied to the device B, and FIG. 22D illustrates a case where a tensile strain is applied to the device B.

It is assumed that the strain formed at locations 86 and 87 of the circular shaped membrane 85 as illustrated in FIG. 21 is virtually in hoop form. As a result, the directions of the strains applied to the two devices A, B will be mutually orthogonal.

As illustrated in FIGS. 22A and 22C, if compressive strains 89, 91 are applied to the devices A, B on the membrane 85, the magnetization direction 65 of the ferromagnetic layer 11, which has a positive magnetostriction coefficient, of one of the devices B will rotate in a direction normal to the compressive strain. The magnetization direction 66 of the ferromagnetic layer 12, which has a negative magnetostriction coefficient, of the other device A will rotate in the opposite direction 94. Therefore, the resistance states of the devices A and B will both be the intermediate resistance state.

On the other hand, if a tensile strain is applied, the opposite response would occur. In other words, as illustrated in FIGS. 22B and 22D, if tensile strains 90, 92 are applied to the devices A, B on the membrane 85, the magnetization direction 65 of the ferromagnetic layer 11, which has a positive magnetostriction coefficient, of one of the devices A will rotate in a direction 96 towards the tensile strain. The magnetization direction 66 of the ferromagnetic layer 12, which has a negative magnetostriction coefficient, of the other device B will rotate in the opposite direction 95. Therefore, the resistance states of the devices A and B will both be the intermediate resistance state.

Next, the effect of the strain sensor according to the thirteenth embodiment will be described.

The strain sensor according to this embodiment can respond to both compressive and tensile strains. Therefore it is possible to provide a strain sensor that can be miniaturized. Also, it can function as a pressure sensor by enabling the membrane to detect external pressure.

Fourteenth Embodiment

Next, a strain sensor according to a fourteenth embodiment will be described.

Figure 23:
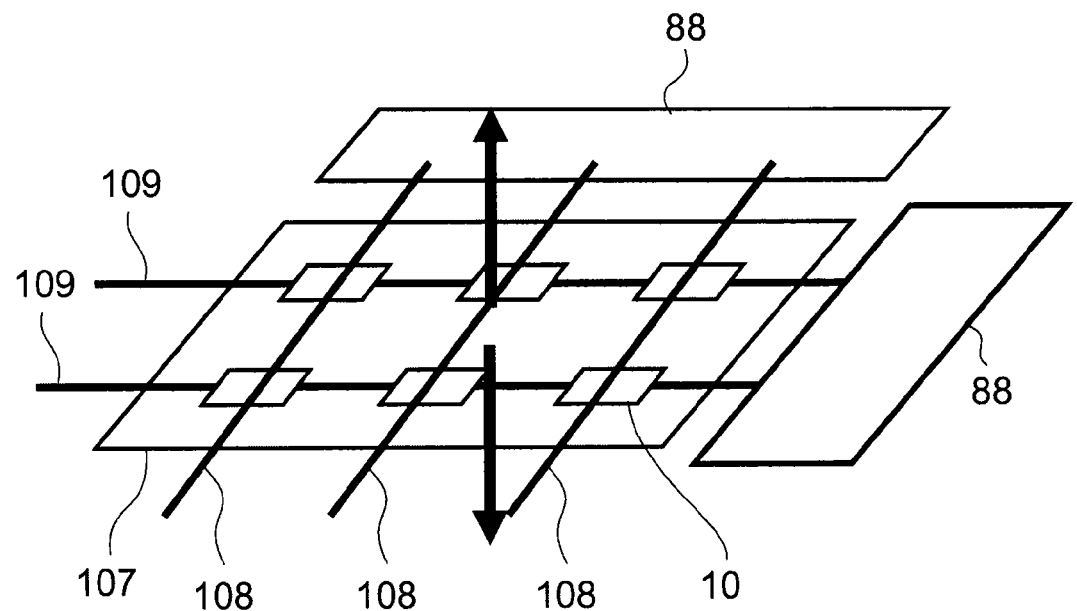
FIG. 23 is a perspective view illustrating a strain sensor according to a fourteenth embodiment.
Figure 24:
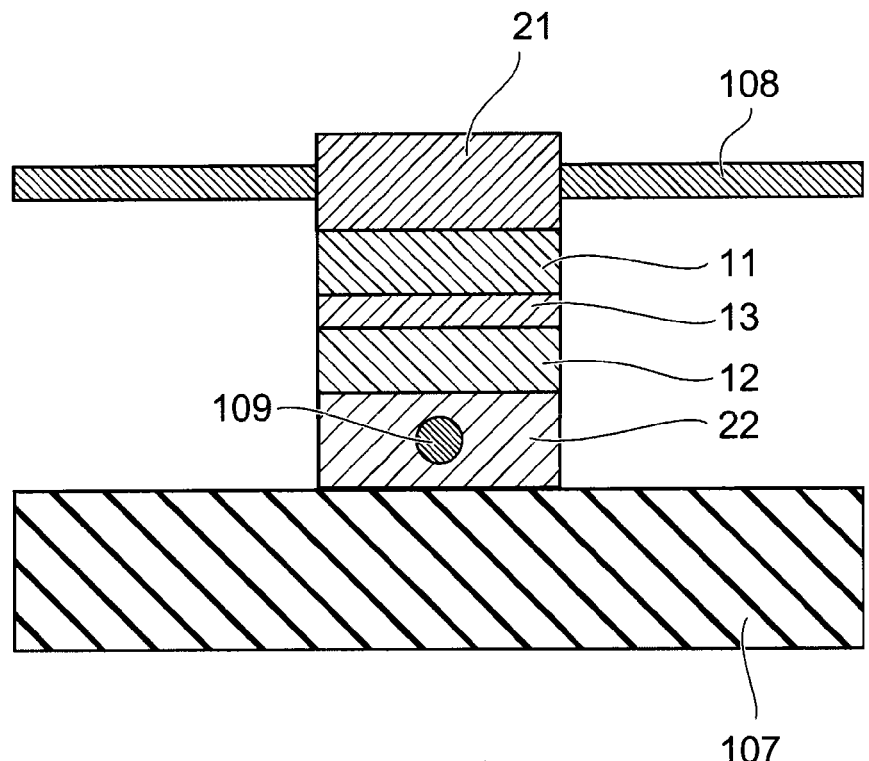
FIG. 24 illustrates a magneto-resistive effect device in the strain sensor according to the fourteenth embodiment.

FIG. 23 is a perspective view illustrating the strain sensor according to the fourteenth embodiment, and FIG. 24 illustrates the magneto-resistive effect device in the strain sensor according to the fourteen embodiments.

As illustrated in FIG. 23, in the strain sensor according to the fourteenth embodiment, a plurality of magneto-resistive effect devices 10 is provided on a flexible substrate 107.

Here the flexible substrate 107 is constituted from a flexible thin film or a flexible sheet that is capable of bending unsymmetrically when viewed from the top surface. The flexible substrate 107 may be supported by a support part at the peripheral portion thereof. These substrates are made from a material that can bend, for example a material whose main component is a polymer. Such a material can include ABS resin, cycloolefin-based resin, ethylene-propylene-based rubber, polyamide, polyamide-imide resin, polybenzimidazole, polybutylene terephthalate, polycarbonate, polyethene, PEEK, polyetherimide, polyethylene imine, polyethylene naphthalate, polyester, polysulfone, polyethylene terephthalate, phenol formaldehyde resin, polyimide, polymethyl methacrylate, polymethylpentene, polyoxymethylene, polypropylene, m-phenyl ether, poly(para-phenylene sulfide), para-aramid, polystyrene, polysulfone, polyvinyl chloride, polytetrafluoroethylene, perfluoroalkoxy, FEP, ETFE, polyethylene chloro trifluoro ethylene, polyvinylidene difluoride, melamine-formaldehyde, liquid crystal polymer, urea-formaldehyde, and so on.

As illustrated in FIG. 23, a plurality of word lines 108 that extend in a certain direction and a plurality of bit lines 109 that extend in a direction that intersects the direction of the word lines in a right angle are provided on the flexible substrate 107.

Also, a plurality of stacked bodies 19 that constitute magneto-resistive effect devices 10 is fixed to the flexible substrate 107. The stacked bodies 19 are connected between each of the plurality of word lines 108 and each of the bit lines 109. The word lines 108 and the bit lines 109 are each electrically connected to a controller 88.

FIG. 24 is a cross-sectional view illustrating the magneto-resistive effect device in the strain sensor according to the fourteenth embodiment.

As illustrated in FIG. 24, the word line 108 is connected to the top electrode 21 of the magneto-resistive effect device 10, and the bit line 109 is connected to the bottom electrode 22. In this embodiment, the sense current flows in the stacking direction of the stacked body 19.

Next, operation of the strain sensor according to the fourteenth embodiment will be described.

In the strain sensor according to the fourteenth embodiment, the word line 108 and the bit line 109 connected to the device 10 at the location on the flexible substrate 107 that is to be measured are selected using the controllers 88, and the resistance state of the device 10 is measured by passing sense current through the selected word line 108 and bit line 109. In this way, the magnitude of the strain at the location where the device 10 is positioned is measured.

Next, the effect of the strain sensor according to the fourteenth embodiment will be described.

In the strain sensor according to this embodiment, the plurality of magneto-resistive effect devices 10 is provided on the flexible substrate 107. Then, it is possible to detect the local strain at the locations where the magneto-resistive effect devices 10 are provided. Therefore it is possible to miniaturize the strain sensor by providing devices 10 that can be miniaturized.

This type of configuration is extremely useful in cases where it is not possible to properly dispose strain sensors at locations where strain is generated. For example, it is extremely useful when used in a blood pressure sensor that is used in daily life, as described later. In a blood pressure sensor that is used in daily life, the sensor is fitted and removed every day, but it is not easy to apply a small sensor to the proper position of the pulse. However, in the case of a sensor array about the size of an adhesive plaster, it is comparatively easy to apply the array on the pulse. In this case, any sensor on the array can measure the pulse, so it is possible to use it for applications in which measurement is extremely difficult, such as measurement of blood pressure every day.

Fifteenth Embodiment

Next, a fifteenth embodiment will be described.

This embodiment relates to a magneto-resistive effect device.

As stated above, in a strain sensor that uses the magneto-resistive effect device 10 according to the first embodiment, it is possible to measure the magnitude of both tensile and compressive strains. However, it is not easy to differentiate between a tensile and a compressive strain.

In the fifteenth embodiment, the above problem is solved with a magneto-resistive effect device to which a third magnetic layer is added, and that includes two spin-valve films.

Figure 25:
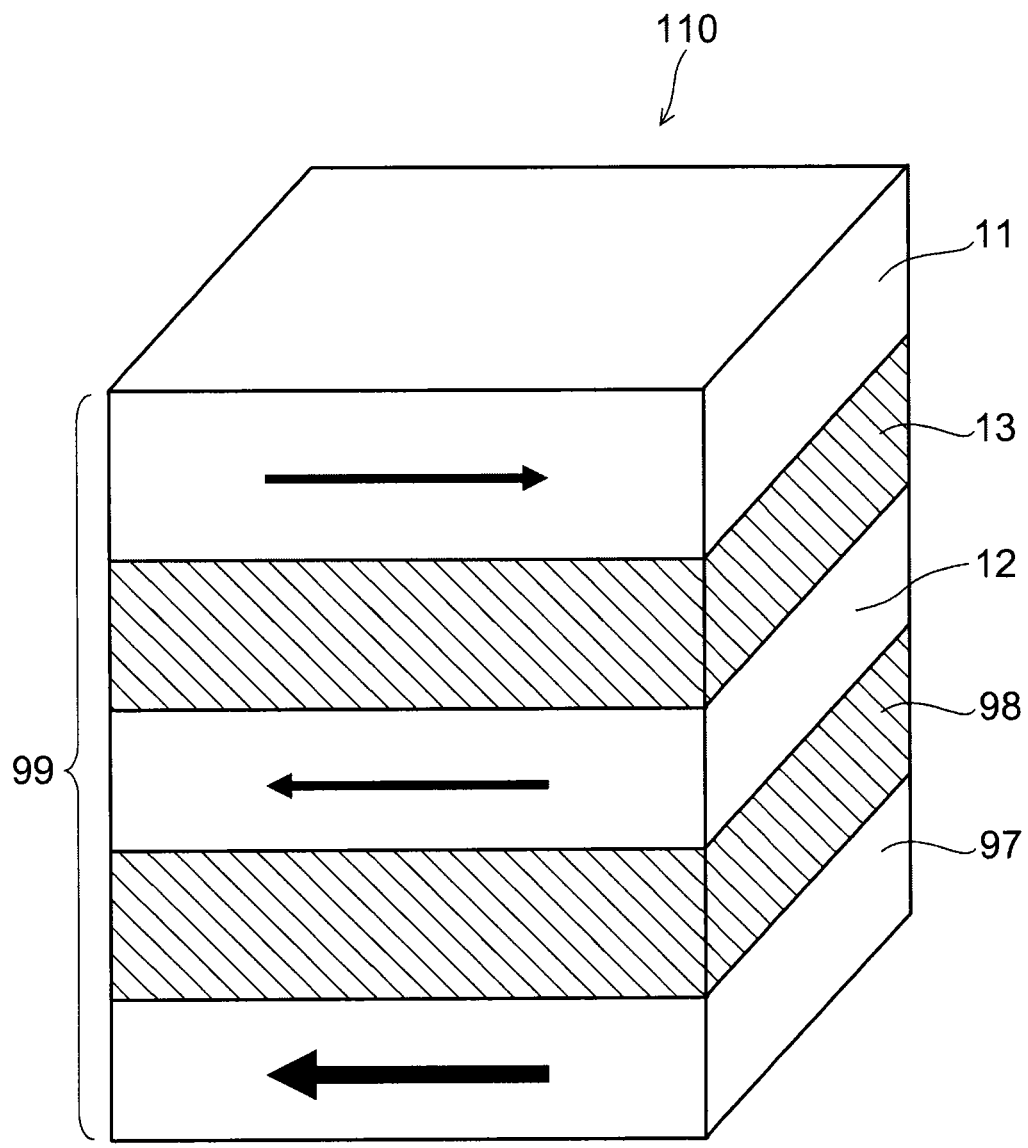
FIG. 25 is a perspective view illustrating a magneto-resistive effect device according to a fifteenth embodiment.

FIG. 25 is a perspective view illustrating the magneto-resistive effect device according to the fifteenth embodiment.

As illustrated in FIG. 25, a third ferromagnetic layer 97 is provided in a magneto-resistive effect device 110. In other words, the spacer layer 13 is provided between the ferromagnetic layer 11 and the ferromagnetic layer 12, and a second spacer layer 98 is provided between the ferromagnetic layer 12 and a third ferromagnetic layer 97, to obtain the structure of a stacked body 99. The third ferromagnetic layer 97 functions as a pinned layer. In other words, the pinned layer functions as a layer whose magnetization direction does not rotate even when a strain is introduced (a pinned reference layer).

Next, operation of the magneto-resistive effect device according to the fifteenth embodiment will be described.

Figure 26A:
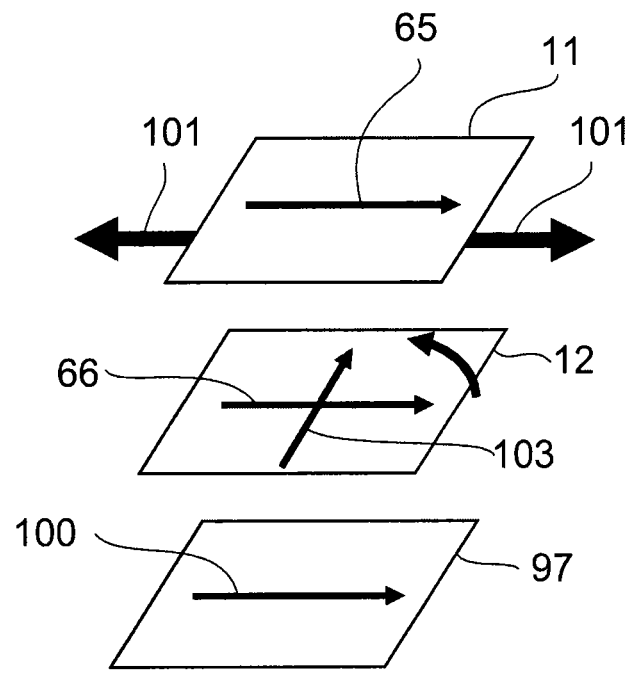
FIGS. 26A and 26B illustrate the stacked body of the magneto-resistive effect device according to the fifteenth embodiment.
Figure 26B:
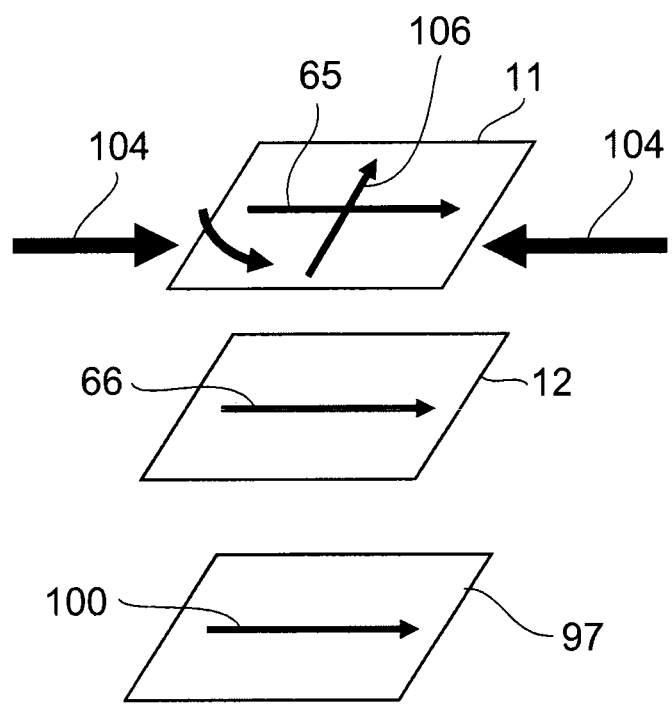

FIGS. 26A and 26B illustrate the stacked body of the magneto-resistive effect device according to the fifteenth embodiment, FIG. 26A illustrates a case of application of a tensile strain, and FIG. 26B illustrates a case of application of a compressive strain.

As illustrated in FIGS. 26A and 26B, in the magneto-resistive effect device 110, among the three ferromagnetic layers, the top layer is the ferromagnetic layer 11 having a positive magnetostriction coefficient, the middle layer is the ferromagnetic layer 12 having a negative magnetostriction coefficient, and the bottom layer is the pinned layer 97. Also, prior to application of the strain, the magnetization directions 65 and 66, and 100 of the ferromagnetic layers 11 and 12 and the pinned layer 97 are parallel. Therefore, prior to application of the strain, the resistance state of the device 110 is the low resistance state.

As illustrated in FIG. 26A, when a tensile strain 101 is applied to the device 110 in the same direction as the magnetization directions 65, 66, and 100, the magnetization direction 65 of the ferromagnetic layer 11 does not change, but the magnetization direction 66 of the ferromagnetic layer 12 changes to a magnetization direction 103 normal to the tensile strain 101. As a result, the resistance state between the ferromagnetic layer 11 and the ferromagnetic layer 12 becomes the intermediate resistance state, the resistance state between the ferromagnetic layer 12 and the pinned layer 97 becomes intermediate resistance state, and overall the resistance state of the device 110 is changed to the high resistance state.

Also, as illustrated in FIG. 26B, when a compressive strain 104 is applied to the device 110 in the same direction as the magnetization directions 65, 66 and 100, the magnetization direction 65 of the ferromagnetic layer 11 changes to a magnetization direction 106 normal to the compressive strain, but the magnetization direction 66 of the ferromagnetic layer 12 does not change. As a result, the resistance state between the ferromagnetic layer 11 and the ferromagnetic layer 12 becomes the intermediate resistance state, the resistance state between the ferromagnetic layer 12 and the pinned layer 97 remains the low resistance state, and overall the resistance state of the device 110 is changed to the intermediate resistance state.

In FIG. 26, the directions of application of the tensile strain and the compressive strain are the same as the magnetization directions of the ferromagnetic layers, but this is not a limitation. The important point is that the magnetization direction of the free layers rotate in opposite directions under the effect of the two types of strain, tensile and compressive.

In this embodiment, there are two spacer layers. One of these, the spacer layer 13, depends on the relative angle between the magnetization directions of the two ferromagnetic layers, and the other spacer layer 98 depends on the relative angle between the magnetization directions of the ferromagnetic layer 12 and the pinned layer 97. Therefore, a difference is produced between the effect of the two types of strain, tensile and compressive.

As illustrated in FIGS. 26A and 26B, in a certain direction a tensile strain can cause the resistance state to change to the high resistance state, and in another direction a compressive strain can cause the resistance state to change to the high resistance state.

Next, the effect of the magneto-resistive effect device according to the fifteenth embodiment will be described.

In the magneto-resistive effect device according to this embodiment, it is possible to distinguish whether the applied strain is a tensile strain or a compressive strain by adding the third ferromagnetic layer, to obtain the magneto-resistive effect device 110 that includes two spin valves. In this way, it is possible to realize a magneto-resistive effect device that is small and is capable of distinguishing the polarity of the strain. The configuration, operation, and effect of this embodiment other than that described above is the same as the first embodiment as described previously.

Sixteenth Embodiment

Next, a sixteenth embodiment will be described.

This embodiment relates to a blood pressure meter.

In this embodiment, a strain sensor according to any of the twelfth through fifteenth embodiments is applied to a blood pressure sensor.

Figure 27:
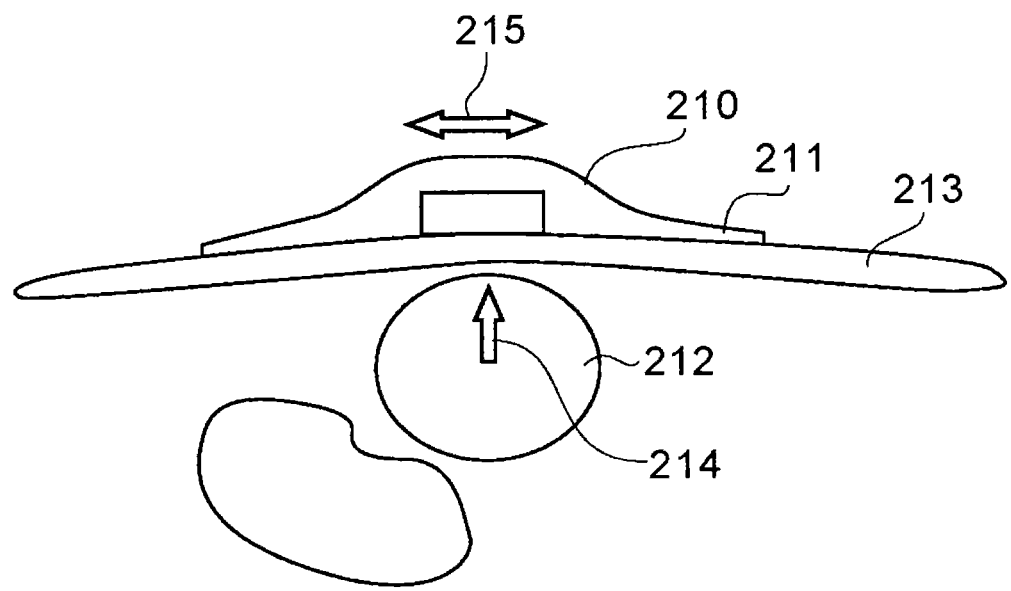
FIG. 27 is a cross-sectional view illustrating a blood pressure sensor according to a sixteenth embodiment.

FIG. 27 is a cross-sectional view illustrating the blood pressure sensor according to the sixteenth embodiment.

As illustrated in FIG. 27, a blood pressure sensor 210 is provided at a blood pressure measurement location, and is provided with a part with the shape of an adhesive plaster 211 for contacting skin surface 213. In other words, the blood pressure sensor 210 is disposed in contact with the skin. The blood pressure sensor 210 is disposed on the skin where there is an artery directly below. The blood flow direction is the direction normal to the plane of the paper. The blood flow direction indicates the direction along which the blood vessels extend. If there is no artery near the surface of the skin, it is difficult to measure the blood pressure. The locations on the surface of the body where the pulse can be detected (and where there are arteries below the surface) are as follows.

Medial bicipital groove (brachial artery), between the flexor carpi radialis tendon and the brachioradialis tendon at the bottom outer forearm (radial artery), between the flexor carpi ulnaris tendon and the superficial digital flexor tendon at the bottom inner forearm (ulnar artery), ulnar extensor pollicis longus muscle tendon (first dorsal metacarpal artery), armpit (axillary artery), femoral trigone (femoral artery), outside of the tendon of the tibialis anterior at the bottom of the front lower leg (anterior tibial artery), lower posterior part of medial malleolus (posterior tibial artery), outside of extensor pollicis longus muscle tendon (dorsal artery of foot), carotid artery triangle (common carotid artery), in front of the insertion of the masseter muscle (facial artery), between the trapezius origins posterior to the sternocleidomastoid insertions (occipital artery), in front of the external acoustic foramen (superficial temporal artery). Therefore, the locations at which the blood pressure sensor 210 are disposed are the above locations. In other words, these correspond to the blood pressure measurement locations. The blood pressure sensor 210 is applied to the surface of the skin at these locations.

Next, operation of the blood pressure sensor according to the sixteenth embodiment will be described.

As illustrated in FIG. 27, when a blood vessel 212 expands in the diametral direction, the skin is pushed up and acts as blood pressure 214. At this time, skin that is in the direction normal to the direction that the blood pressure 214 acts is subject to a tensile stress 215. At the same time, it acts on the blood pressure sensor 210 in the direction of the tensile stress 215.

Figure 28:
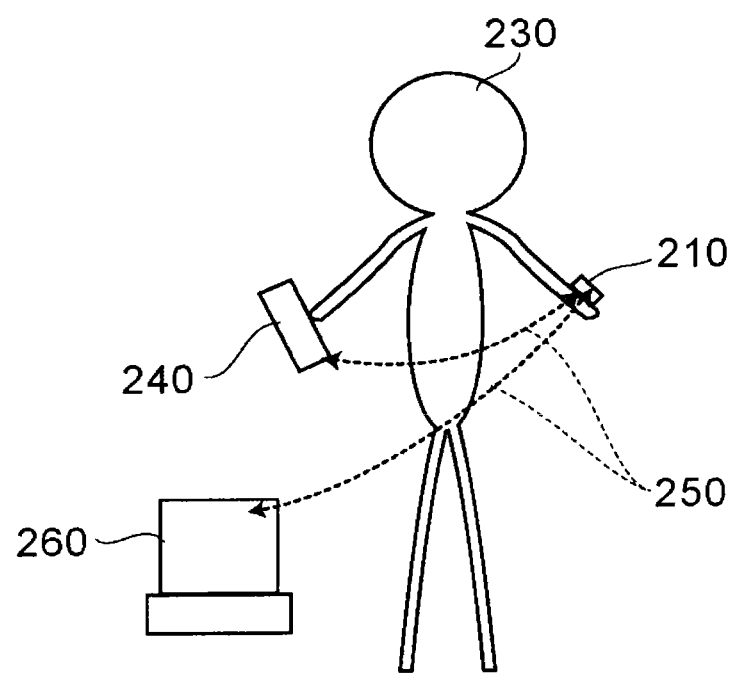
FIG. 28 illustrates the blood pressure sensor according to the sixteenth embodiment.

FIG. 28 illustrates the blood pressure sensor according to the sixteenth embodiment.

As illustrated in FIG. 28, the blood pressure of a subject 230 is measured using the blood pressure sensor 210. The blood pressure sensor 210 is applied to a blood pressure measurement location, for example a wrist.

A small battery can be used as the method of supplying electricity to the blood pressure sensor 210. Also, electricity can be supplied by wireless 250.

The method of accumulating the blood pressure sensor 210 data can be transmission by wireless 250, and accumulation in a mobile phone 240, a personal computer 260, a wrist watch, or the like.

Next, the effect of the blood pressure sensor according to the sixteenth embodiment will be described.

The blood pressure sensor 210 according to this embodiment includes the magneto-resistive effect device 10 or 110 which is suitable for high densification, so it can be miniaturized. Therefore it can be used as an ubiquitous health monitoring device that can be carried around while walking. In this way it is possible to monitor the blood pressure values of a person or animal.

Seventeenth Embodiment

Next, a seventeenth embodiment will be described.

This embodiment relates to a blood pressure measuring system.

Figure 29:
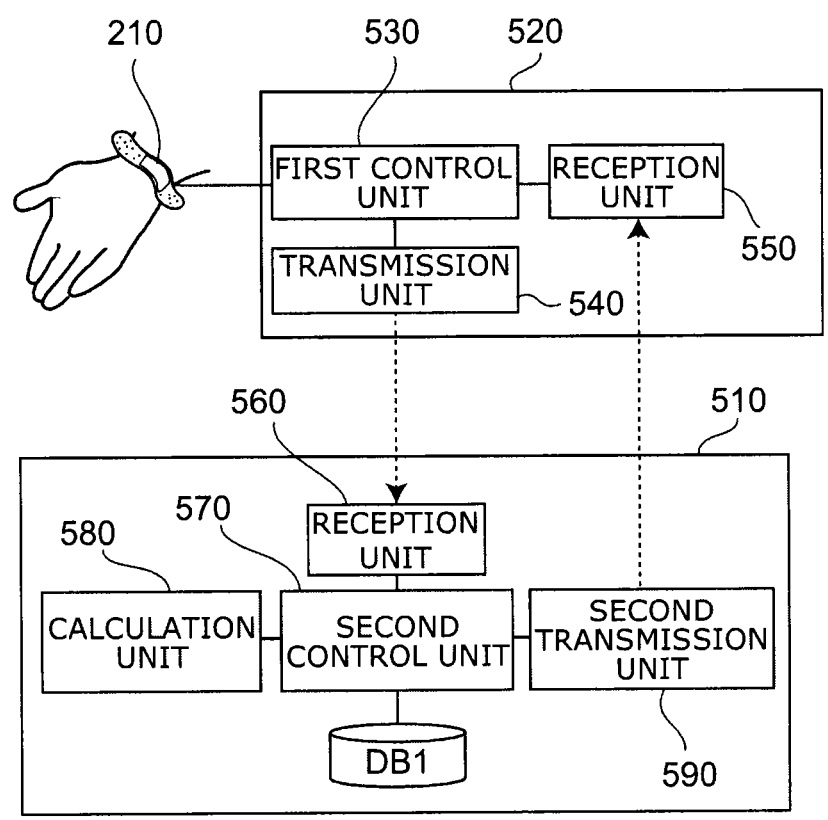
FIG. 29 illustrates a blood pressure measuring system according to a seventeenth embodiment.

FIG. 29 illustrates the blood pressure measuring system according to the seventeenth embodiment.

As illustrated in FIG. 29, the blood pressure sensor 210 and electronic equipment 510 is provided in the blood pressure measurement system according to this embodiment. The blood pressure sensor 210 is fitted to a blood pressure measurement location of a subject. Here the blood pressure measurement location is illustrated as the wrist. The electronic equipment 510 can include, for example, a television, a mobile phone, a medical database, and a personal computer.

An internal processing unit 520 is provided in the blood pressure sensor 210.

The processing unit 520 includes a first control unit 530 that controls the blood pressure sensor 210, a transmission unit 540 that transmits information from the first control unit 530 externally, and a second reception unit 550 that receives information from the outside and transmits it to the first control unit 530. The information includes data on blood pressure values, data on rates of change in electrical resistance, and data on electrical resistance values.

The electronic equipment 510 includes a reception unit 560, a second control unit 570, a calculation unit 580, a second transmission unit 590, and a database (hereafter referred to as "DB 1").

The reception unit 560 receives information transmitted from the transmission unit 540 and transmits it to the second control unit 570.

The second control unit 570 transmits the information received from the reception unit 560 to the calculation unit 580, transmits it to the second transmission unit 590, or stores the information in the DB 1 as data.

The calculation unit 580 carries out calculations on the information transmitted from the second control unit 570.

Exchange of information between the transmission unit 540 and the reception unit 560, and exchange of information between the second transmission unit 590 and the reception unit 550 can be by wireless transmission or by cable transmission.

Next, the operation of the blood pressure measurement system according to the seventeenth embodiment will be described.

Figure 30:
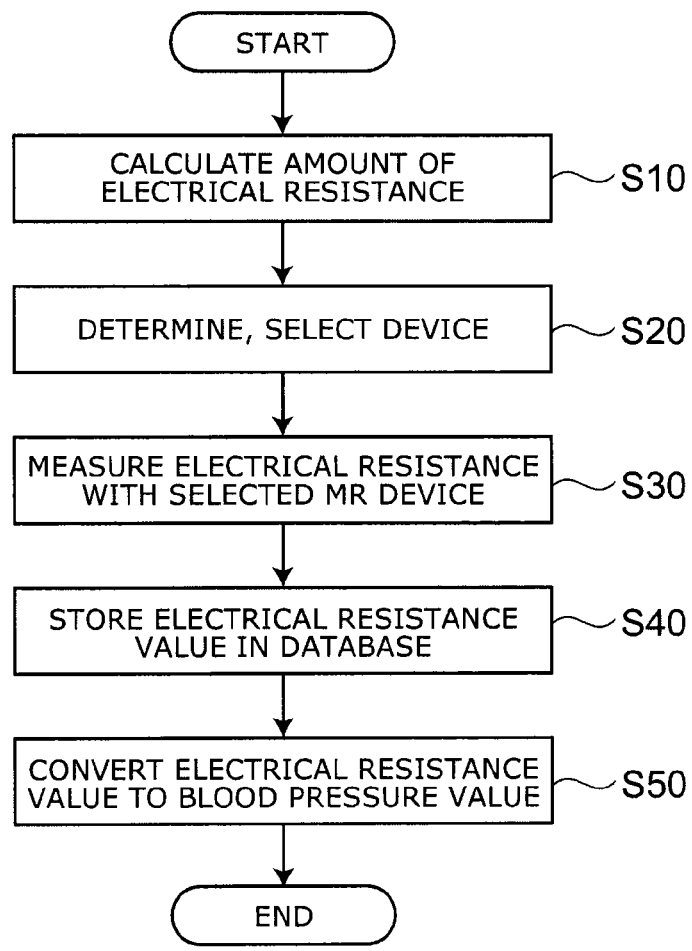
FIG. 30 is a flowchart showing the operation of the blood pressure measurement system according to the seventeenth embodiment.

FIG. 30 is a flowchart showing the operation of the blood pressure measurement system.

As illustrated in FIG. 30, in step S10, the first control unit 530 instructs the blood pressure sensor 210 to measure the amount of change in electrical resistance at the blood pressure measurement location. At this time, the amount of change in electrical resistance in all the magneto-resistive effect devices provided in the blood pressure sensor 210 is measured.

Next, in step S20, the first control unit 530 determines and selects the magneto-resistive effect device (MR device) on the blood pressure measurement location that is to be measured. Then, in step S30, the electrical resistance of the selected MR device is measured. Next, in step S40, the transmission unit 540 transmits the measured electrical resistance value to the electronic equipment 510. The second control unit 570 stores the received electrical resistance value data in the database DB 1. Then, in step S50, the second control unit 570 transmits the electrical resistance value received by the reception unit 560 to the calculation unit 580. The calculation unit 580 converts the electrical resistance value to a blood pressure value.

Next, the effect of the blood pressure measurement system according to the seventeenth embodiment will be described.

The blood pressure measurement system according to this embodiment includes the magneto-resistive effect device which is suitable for high densification, so it can be miniaturized. Therefore it can be used as an ubiquitous health monitoring device that can be carried around while walking.

Eighteenth Embodiment

Next, a eighteenth embodiment will be described.

This embodiment relates to an air pressure meter.

In this embodiment, the strain sensor that incorporates the magneto-resistive effect device 110 according to the fifteenth embodiment is applied to an air pressure meter. The strain sensor in which the magneto-resistive effect device 110 according to the fifteenth embodiment is provided can distinguish between tensile strain and compressive strain. Also, it can be miniaturized. For example, the air pressure meter according to this embodiment that includes this strain sensor is miniature, so it can be provided on the surface or back face of a wing of an aircraft. Also, this air pressure meter can distinguish between negative pressure and positive pressure, so it can properly measure the changes in pressure produced on the surface or back face of the wing, so it is possible to know if the aircraft stalls or spins.

Nineteenth Embodiment

Next a nineteenth embodiment will be described.

This embodiment relates to a structural health monitoring sensor.

Figure 31:
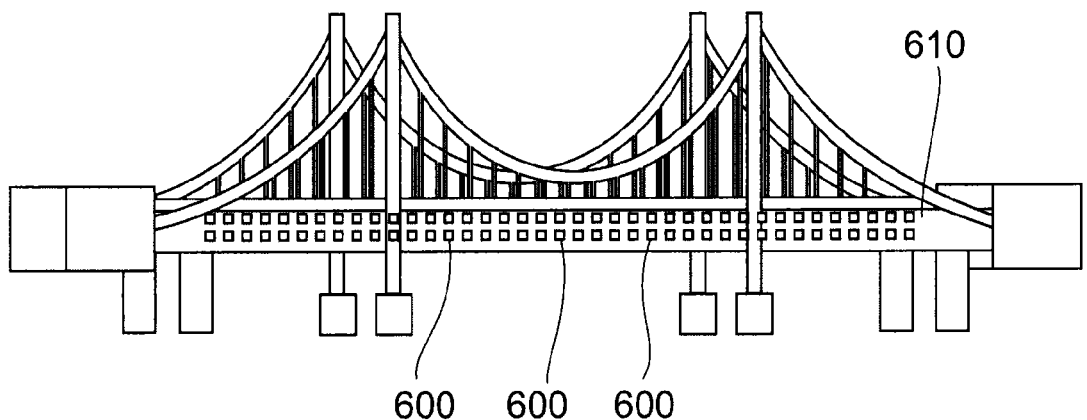
FIG. 31 illustrates a structural health monitoring sensor according to a nineteenth embodiment.
Figure 32:
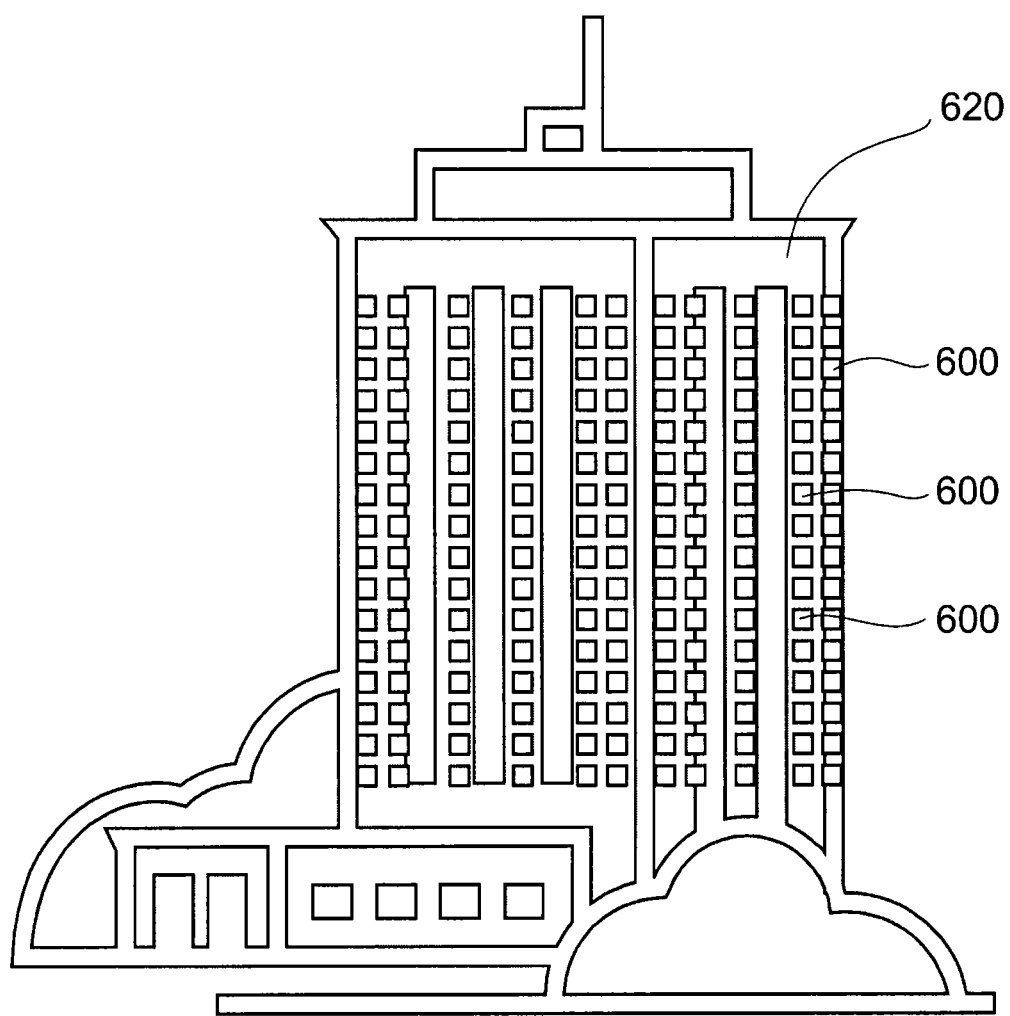
FIG. 32 illustrates the structural health monitoring sensor according to the nineteenth embodiment.

FIGS. 31 and 32 illustrate the structural health monitoring sensor according to the nineteenth embodiment.

As illustrated in FIG. 31, a plurality of structural health monitoring sensors 600 is provided on a surface of a bridge beam 610 of a suspension bridge.

Also, as illustrated in FIG. 32, a plurality of structural health monitoring sensors 600 is provided on the surface of an external wall 620 of a building. Strain sensors according to the twelfth through fifteenth embodiments are used in the structural health monitoring sensor 600 according to this embodiment. It can be easily checked periodically using the structural health monitoring sensors 600 whether strains have occurred in the bridge beam 610 or the external wall 620 of the building that are different from the initial state.

According to the embodiments as explained above, it is possible to provide a magneto-resistive effect device, a magnetic head assembly, a strain sensor, a pressure sensor, a blood pressure sensor, and a structural health monitoring sensor that is suitable for high densification.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modification as would fall within the scope and spirit of the inventions.

What is claimed is:

1. A strain sensor comprising:
   a substrate being deformable;
   a first electrode;
   a second electrode provided between the first electrode and the substrate; and
   a stacked body including
      a first magnetic layer provided between the first electrode and the second electrode, the first magnetic layer having a first magnetization,
      a second magnetic layer provided between the first magnetic layer and the second electrode, the second magnetic layer having a second magnetization, and
      a first spacer layer provided between the first magnetic layer and the second magnetic layer,
   wherein
   the first and second electrodes supply to the stacked body current that flows along a stacking direction of the stacked body, the first magnetization changes in accordance with a first external strain applied to the stacked body, the first external strain has a first component along a first direction, the external strain is generated by a deformation of the substrate to cause a resistance between the first and second electrodes to be changed,
   the second magnetization changes in accordance with a second external strain applied to the stacked body, the second external strain has a second component along a second direction different from the first direction, the second external strain is generated by the deformation, and
   the first and second external strains are detected by the change in the resistance.

2. The strain sensor according to claim 1, wherein the first magnetic layer has a positive magnetostriction coefficient, and the second magnetic layer has a negative magnetostriction coefficient.

3. The strain sensor according to claim 1, wherein in a state where the first external strain is not applied, the first magnetization is parallel or antiparallel with the second magnetization.

4. The strain sensor according to claim 1, wherein the first magnetic layer has an oxide layer including one or more metals selected from the group consisting of iron, cobalt, and nickel.

5. The strain sensor according to claim 1, wherein the second magnetic layer includes one or more metals selected from the group consisting of nickel and samarium iron (SmFe).

6. The strain sensor according to claim 1, wherein the first spacer layer includes at least one of an oxide of one metal selected from the group consisting of aluminum, titanium, zinc, silicon, hafnium, tantalum, molybdenum, tungsten, niobium, chromium, magnesium, and zirconium, and a nitride of one metal selected from the group consisting of aluminum, titanium, zinc, silicon, hafnium, tantalum, molybdenum, tungsten, niobium, chromium, magnesium, and zirconium.

7. The strain sensor according to claim 1, further comprising a third magnetic layer; and
   a second spacer layer,
   the second magnetic layer being disposed between the first spacer layer and the third magnetic layer,
   the third magnetic layer having a third magnetization being fixed, and
   the second spacer layer being provided between the second magnetic layer and the third magnetic layer.

8. The strain sensor according to claim 1, wherein the substrate includes
   a membrane being deformable, and
   a support part supporting the membrane,
   the stacked body is provided between the membrane and the first electrode, and
   the second electrode is provided between the membrane and the stacked body.

9. The strain sensor according to claim 1, further comprising
   a plurality of word lines extending in a fourth direction crossing a third direction from the first magnetic layer toward the second magnetic layer; and
   a plurality of bit lines extending in a fifth direction crossing the fourth direction and the third direction,
   the stacked body being provided in a plurality,
   each of the stacked bodies being connected with one of the plurality of word lines and one of the plurality of bit lines.

10. The strain sensor according to claim 1, wherein the first magnetic layer has a first composition including one or more metals selected from the group consisting of iron, cobalt, and nickel, and
    the second magnetic layer has a composition different from the first composition.

11. The strain sensor according to claim 1, wherein the second direction is opposite to the first direction.

12. A pressure sensor, comprising:
    a strain sensor including:
       a substrate including:
          a membrane being deformable, and
          a support part supporting the membrane;

a first electrode;

a second electrode provided between the first electrode and the membrane;

a stacked body including a first magnetic layer provided between the first electrode and the second electrode, the first magnetic layer having a first magnetization, a second magnetic layer provided between the first magnetic layer and the second electrode, the second magnetic layer having a second magnetization, and a first spacer layer provided between the first magnetic layer and the second magnetic layer, wherein the first and second electrodes supply to the stacked body current that flows along a stacking direction of the stacked body, the first magnetization changes in accordance with a first external strain applied to the stacked body, the first external strain has a first component along a first direction, the external strain is generated by a deformation of the membrane to cause a resistance between the first and second electrodes to be changed, the second magnetization changes in accordance with a second external strain applied to the stacked body, the second external strain has a second component along a second direction different from the first direction, the second external strain is generated by the deformation, the first and second external strains are detected by the change in the resistance, and an external pressure is detected by detecting the external strain generated by the external pressure.

13. The pressure sensor according to claim 12, wherein the first magnetic layer has a first composition including one or more metals selected from the group consisting of iron, cobalt, and nickel, and the second magnetic layer has a composition different from the first composition.

14. The pressure sensor according to claim 12, wherein the second direction is opposite to the first direction.

15. A blood pressure sensor configured to monitor a blood pressure of a person or an animal, the blood pressure sensor comprising:

a strain sensor including:
a substrate being deformable;
a first electrode;
a second electrode provided between the first electrode and the substrate; and
a stacked body including
a first magnetic layer provided between the first electrode and the second electrode, the first magnetic layer having a first magnetization,
a second magnetic layer provided between the first magnetic layer and the second electrode, the second magnetic layer having a second magnetization, and
a first spacer layer provided between the first magnetic layer and the second magnetic layer, wherein the first and second electrodes supply to the stacked body current that flows along a stacking direction of the stacked body, the first magnetization changes in accordance with a first external strain applied to the stacked body, the first external strain has a first component along a first direction, the external strain is generated by a deformation of the substrate to cause a resistance between the first and second electrodes to be changed, the second magnetization changes in accordance with a second external strain applied to the stacked body, the second external strain has a second component along a second direction different from the first direction, the second external strain is generated by the deformation, the first and second external strains are detected by the change in the resistance, and a blood pressure is detected by detecting the external strain generated by the blood pressure.

16. The blood pressure sensor according to claim 15, wherein the first magnetic layer has a first composition including one or more metals selected from the group consisting of iron, cobalt, and nickel, and the second magnetic layer has a composition different from the first composition.

17. The blood pressure sensor according to claim 15, the second direction is opposite to the first direction.

18. A structural health monitoring sensor configured to perform structural condition monitoring to monitor a strain state of a bridge or building structure, the structural health monitoring sensor comprising:

a strain sensor including:
a substrate being deformable;
a first electrode;
a second electrode provided between the first electrode and the substrate; and
a stacked body including
a first magnetic layer provided between the first electrode and the second electrode, the first magnetic layer having a first magnetization,
a second magnetic layer provided between the first magnetic layer and the second electrode, the second magnetic layer having a second magnetization, and
a first spacer layer provided between the first magnetic layer and the second magnetic layer, wherein the first and second electrodes supply to the stacked body current that flows along a stacking direction of the stacked body, the first magnetization changes in accordance with a first external strain applied to the stacked body, the first external strain has a first component along a first direction, the external strain is generated by a deformation of the substrate to cause a resistance between the first and second electrodes to be changed, the second magnetization changes in accordance with a second external strain applied to the stacked body, the second external strain has a second component along a second direction different from the first direction, the second external strain is generated by the deformation, the first and second external strains are detected by the change in the resistance, and the first and second external strains are changed in accordance with a change of a strain state.

19. The structural health monitoring sensor according to claim 18, wherein the first magnetic layer has a first composition including one or more metals selected from the group consisting of iron, cobalt, and nickel, and the second magnetic layer has a composition different from the first composition.

20. The structural health monitoring sensor according to claim 18, wherein the second direction is opposite to the first direction.

21. A strain sensor comprising:
a substrate being deformable;
a first electrode;
a second electrode provided between the first electrode and the substrate; and
a stacked body including
a first magnetic layer provided between the first electrode and the second electrode, the first magnetic layer having a first magnetization,
a second magnetic layer provided between the first magnetic layer and the second electrode, the second magnetic layer having a second magnetization, and
a first spacer layer provided between the first magnetic layer and the second magnetic layer,
wherein
the first and second electrodes supply to the stacked body current that flows along a stacking direction of the stacked body,
the first magnetization changes in accordance with a first external strain applied to the stacked body, the external strain is generated by a deformation of the substrate to cause a resistance between the first and second electrodes to be changed,
the second magnetization changes in accordance with a second external strain applied to the stacked body, the second external strain is generated by the deformation,
the first external strain is one of a tensile strain and a compressive strain,
the second external strain is the other of the tensile strain and the compressive strain, and
the first and second external strains are detected by the change in the resistance.

22. A pressure sensor, comprising:
a strain sensor including
a substrate including
a membrane being deformable, and
a support part supporting the membrane;
a first electrode;
a second electrode provided between the first electrode and the membrane,
a stacked body including
a first magnetic layer provided between the first electrode and the second electrode, the first magnetic layer having a first magnetization,
a second magnetic layer provided between the first magnetic layer and the second electrode, the second magnetic layer having a second magnetization, and
a first spacer layer provided between the first magnetic layer and the second magnetic layer, and
wherein
the first and second electrodes supply to the stacked body current that flows along a stacking direction of the stacked body,
the first magnetization changes in accordance with a first external strain applied to the stacked body, the external strain is generated by a deformation of the membrane to cause a resistance between the first and second electrodes to be changed,
the second magnetization changes in accordance with a second external strain applied to the stacked body, the second external strain is generated by the deformation,
the first external strain is one of a tensile strain and a compressive strain,
the second external strain is the other of the tensile strain and the compressive strain,
the first and second external strains are detected by the change in the resistance, and
an external pressure is detected by detecting the external strain generated by the external pressure.

23. A blood pressure sensor configured to monitor a blood pressure of a person or an animal, the blood pressure sensor comprising:
a strain sensor including:
a substrate being deformable;
a first electrode;
a second electrode provided between the first electrode and the substrate; and
a stacked body including
a first magnetic layer provided between the first electrode and the second electrode, the first magnetic layer having a first magnetization,
a second magnetic layer provided between the first magnetic layer and the second electrode, the second magnetic layer having a second magnetization, and
a first spacer layer provided between the first magnetic layer and the second magnetic layer,
wherein
the first and second electrodes supply to the stacked body current that flows along a stacking direction of the stacked body,
the first magnetization changes in accordance with a first external strain applied to the stacked body, the external strain is generated by a deformation of the substrate to cause a resistance between the first and second electrodes to be changed,
the second magnetization changes in accordance with a second external strain applied to the stacked body, the second external strain is generated by the deformation,
the first external strain is one of a tensile strain and a compressive strain,
the second external strain is the other of the tensile strain and the compressive strain,
the first and second external strains are detected by the change in the resistance, and
a blood pressure is detected by detecting the external strain generated by the blood pressure.

24. A structural health monitoring sensor configured to perform structural condition monitoring to monitor a strain state of a bridge or building structure, the structural health monitoring sensor comprising:
a strain sensor including:
a substrate being deformable;
a first electrode;
a second electrode provided between the first electrode and the substrate; and
a stacked body including
a first magnetic layer provided between the first electrode and the second electrode, the first magnetic layer having a first magnetization,
a second magnetic layer provided between the first magnetic layer and the second electrode, the second magnetic layer having a second magnetization, and
a first spacer layer provided between the first magnetic layer and the second magnetic layer,
wherein
the first and second electrodes supply to the stacked body current that flows along a stacking direction of the stacked body,
the first magnetization changes in accordance with a first external strain applied to the stacked body, the external strain is generated by a deformation of the substrate to cause a resistance between the first and second electrodes to be changed, the second magnetization changes in accordance with a second external strain applied to the stacked body, the second external strain is generated by the deformation, the first external strain is one of a tensile strain and a compressive strain, the second external strain is the other of the tensile strain and the compressive strain, the first and second external strains are detected by the change in the resistance, and the first and second external strains are changed in accordance with a change of a strain state.

* * * * *